United States Patent
Pandey et al.

(10) Patent No.: US 10,874,333 B2
(45) Date of Patent: Dec. 29, 2020

(54) SYSTEMS AND METHODS FOR DIAGNOSIS OF MIDDLE EAR CONDITIONS AND DETECTION OF ANALYTES IN THE TYMPANIC MEMBRANE

(71) Applicants: Massachusetts Institute of Technology, Cambridge, MA (US); Connecticut Children's Medical Center, Hartford, CT (US)

(72) Inventors: Rishikesh Pandey, Arlington, MA (US); Nicolas Spegazzini, Arlington, MA (US); Luis H. Galindo, Fitchburg, MA (US); Ramachandra Dasari, Shererville, IN (US); Tulio Alberto Valdez, Simsbury, CT (US)

(73) Assignees: Massachusetts Institute of Technology, Cambridge, MA (US); Connecticut Children's Medical Center, Hartford, CT (US)

( * ) Notice: Subject to any disclaimer, the term of this patent is extended or adjusted under 35 U.S.C. 154(b) by 460 days.

(21) Appl. No.: 15/267,057

(22) Filed: Sep. 15, 2016

(65) Prior Publication Data
US 2017/0071509 A1 Mar. 16, 2017

Related U.S. Application Data

(60) Provisional application No. 62/218,989, filed on Sep. 15, 2015.

(51) Int. Cl.
*A61B 5/00* (2006.01)
*A61B 5/12* (2006.01)
(Continued)

(52) U.S. Cl.
CPC ............ *A61B 5/12* (2013.01); *A61B 1/00009* (2013.01); *A61B 1/00045* (2013.01);
(Continued)

(58) Field of Classification Search
CPC ....... A61B 5/12; A61B 5/6817; A61B 5/0084; A61B 5/0075; A61B 5/1459;
(Continued)

(56) References Cited

U.S. PATENT DOCUMENTS

| 5,115,133 A | 5/1992 | Knudson |
| 5,666,956 A | 9/1997 | Buchert |

(Continued)

FOREIGN PATENT DOCUMENTS

| WO | 2006112837 A1 | 10/2006 |
| WO | 2009157825 A1 | 12/2009 |
| WO | 2015021300 A1 | 2/2015 |

OTHER PUBLICATIONS

Levy, Lauren L., et al. "Optical imaging with a high-resolution microendoscope to identify cholesteatoma of the middle ear." The Laryngoscope 123.4 (Jan. 8, 2013): 1016-1020.
(Continued)

*Primary Examiner* — Navin Natnithithadha
*Assistant Examiner* — Andrey Shostak
(74) *Attorney, Agent, or Firm* — McCarter & English, LLP

(57) ABSTRACT

Systems and methods are presented for the diagnosis of middle ear pathological conditions based on spectral signatures. Preferred embodiments provide for detection of one or more analytes from the tympanic membrane. Devices use spectral measurements including spectral imaging to non-invasively identify middle ear pathological conditions including cholesteatoma and acute otitis media by providing real-time information of differentially expressed molecules. Devices and methods can also be used to non-invasively detect and quantify blood analytes from the tympanic membrane.

38 Claims, 26 Drawing Sheets

(51) Int. Cl.
| | |
|---|---|
| A61B 5/1459 | (2006.01) |
| A61B 1/07 | (2006.01) |
| A61B 1/227 | (2006.01) |
| A61B 1/00 | (2006.01) |
| A61B 5/145 | (2006.01) |
| A61B 1/04 | (2006.01) |
| A61B 1/32 | (2006.01) |
| A61B 1/06 | (2006.01) |
| G01N 21/65 | (2006.01) |
| G01J 3/44 | (2006.01) |
| G01J 3/02 | (2006.01) |
| G01N 21/64 | (2006.01) |

(52) U.S. Cl.
CPC .......... A61B 1/043 (2013.01); A61B 1/0638 (2013.01); A61B 1/0684 (2013.01); A61B 1/07 (2013.01); A61B 1/227 (2013.01); A61B 1/32 (2013.01); A61B 5/0075 (2013.01); A61B 5/0084 (2013.01); A61B 5/1459 (2013.01); A61B 5/14532 (2013.01); A61B 5/14546 (2013.01); A61B 5/6817 (2013.01); A61B 5/7282 (2013.01); G01J 3/0218 (2013.01); G01J 3/44 (2013.01); G01J 3/4406 (2013.01); G01N 21/65 (2013.01); A61B 5/0071 (2013.01); G01N 21/6486 (2013.01)

(58) Field of Classification Search
CPC .............. A61B 5/7282; A61B 5/14546; A61B 5/14532; A61B 5/0071; A61B 1/0638; A61B 1/07; A61B 1/043; A61B 1/0684; A61B 1/32; A61B 1/00045; A61B 1/00009; A61B 1/227; G01J 3/0218; G01J 3/4406; G01J 3/44; G01N 21/65; G01N 21/6486
See application file for complete search history.

(56) References Cited

U.S. PATENT DOCUMENTS

| | | | |
|---|---|---|---|
| 5,823,966 | A | 10/1998 | Buchert |
| 6,002,953 | A | 12/1999 | Block |
| 6,181,957 | B1 | 1/2001 | Lambert et al. |
| 6,377,828 | B1 | 4/2002 | Chaiken et al. |
| 6,379,920 | B1 | 4/2002 | El-Sayed et al. |
| 6,574,501 | B2 | 6/2003 | Lambert et al. |
| 6,990,364 | B2 | 1/2006 | Ruchti et al. |
| 7,039,446 | B2 | 5/2006 | Ruchti et al. |
| 7,399,275 | B2 | 7/2008 | Goldfain et al. |
| 7,509,153 | B2 | 3/2009 | Blank et al. |
| 7,684,841 | B2 | 3/2010 | Shioi |
| 8,066,634 | B2 | 11/2011 | Andreassen et al. |
| 8,115,934 | B2 | 2/2012 | Boppart et al. |
| 8,355,767 | B2 | 1/2013 | Hunter et al. |
| 8,364,218 | B2 | 1/2013 | Gerlitz |
| 8,515,506 | B2 | 8/2013 | Ridder et al. |
| 8,858,430 | B2 | 10/2014 | Oyadiran et al. |
| 10,006,922 | B2 | 6/2018 | Dasari et al. |
| 2004/0166495 | A1* | 8/2004 | Greinwald, Jr. ..... C12Q 1/6883 435/6.15 |
| 2007/0060806 | A1* | 3/2007 | Hunter ............... A61B 5/14532 600/316 |
| 2007/0112273 | A1* | 5/2007 | Rogers .................. A61B 1/227 600/475 |
| 2007/0167836 | A1 | 7/2007 | Scepanovic et al. |
| 2008/0009688 | A1 | 1/2008 | Dahlen et al. |
| 2010/0016689 | A1 | 1/2010 | Kanayama et al. |
| 2010/0208252 | A1 | 8/2010 | Marks et al. |
| 2011/0224493 | A1 | 9/2011 | Oyadiran et al. |
| 2012/0035442 | A1 | 2/2012 | Barman et al. |
| 2012/0302892 | A1* | 11/2012 | Lue ..................... A61B 5/0071 600/476 |
| 2013/0023914 | A1* | 1/2013 | Truong ............. A61B 1/00087 606/162 |
| 2014/0349337 | A1 | 11/2014 | Dasari et al. |
| 2015/0044098 | A1 | 2/2015 | Smart et al. |
| 2015/0305609 | A1* | 10/2015 | Hoberman ............ G06T 7/0012 382/128 |
| 2016/0007840 | A1* | 1/2016 | Boppart .............. A61B 5/0075 600/188 |
| 2017/0248523 | A1* | 8/2017 | Hasegawa ............ G01N 21/658 |

OTHER PUBLICATIONS

Longo, Kaitlyn M., "Bimodal Approach Using Spectroscopy and Digitial Imaging to Assist Otitis Media Diagnosis." Master's Thesis. Paper 594. University of Connecticut—Storrs; Completed May 8, 2014, accessible after embargo beginning May 8, 2015; Accessed on the Internet at http://digitalcommons.uconn.edu/gs_theses/594.

Longo, Kaitlyn, Donald Peterson, and Tulio A. Valdez. "Bi modal approach using spectroscopy and digital imaging to assist otitis media diagnosis." 40th Annual Northeast Bioengineering Conference (NEBEC). IEEE, Apr. 25, 2014.

Malchoff, Carl D., et al. "A novel noninvasive blood glucose monitor." Diabetes Care 25.12 (Dec. 2002): 2268-2275.

Monroy, Guillermo L., et al. "Noninvasive depth-resolved optical measurements of the tympanic membrane and middle ear for differentiating otitis media." The Laryngoscope 125.8 (Jan. 19, 2015): E276-E282.

Muldoon, Timothy J., et al. "Subcellular-resolution molecular imaging within living tissue by fiber microendoscopy." Optics express 15.25 (Nov. 27, 2007): 16413-16423.

Pandey, Rishikesh, et al. "Discerning the differential molecular pathology of proliferative middle ear lesions using Raman spectroscopy." Scientific reports 5:13305 (Aug. 20, 2015).

Singh, Gajendra Pratap, "Raman Otoscope and Raman earband", accessed on the Internet at http://web.mit.edu/gpsingh/www/Raman%20otoscope%20and%20Raman%20earband.pdf (retrieved Sep. 21, 2016).

Spegazzini, Nicolas, et al. "Spectroscopic approach for dynamic bioanalyte tracking with minimal concentration information." Scientific reports 4 (Nov. 12, 2014): 7013.

Valdez, Tulio A., et al. "Multiwavelength fluorescence otoscope for video-rate chemical imaging of middle ear pathology." Analytical chemistry 86.20 (Sep. 16, 2014): 10454-10460.

International Search Report for Application No. PCT/US2016/051998, dated Dec. 21, 2016. 5 pages.

International Preliminary Report on Patentability for Application No. PCT/US2016/051998, dated Mar. 29, 2018. 9 pages.

* cited by examiner

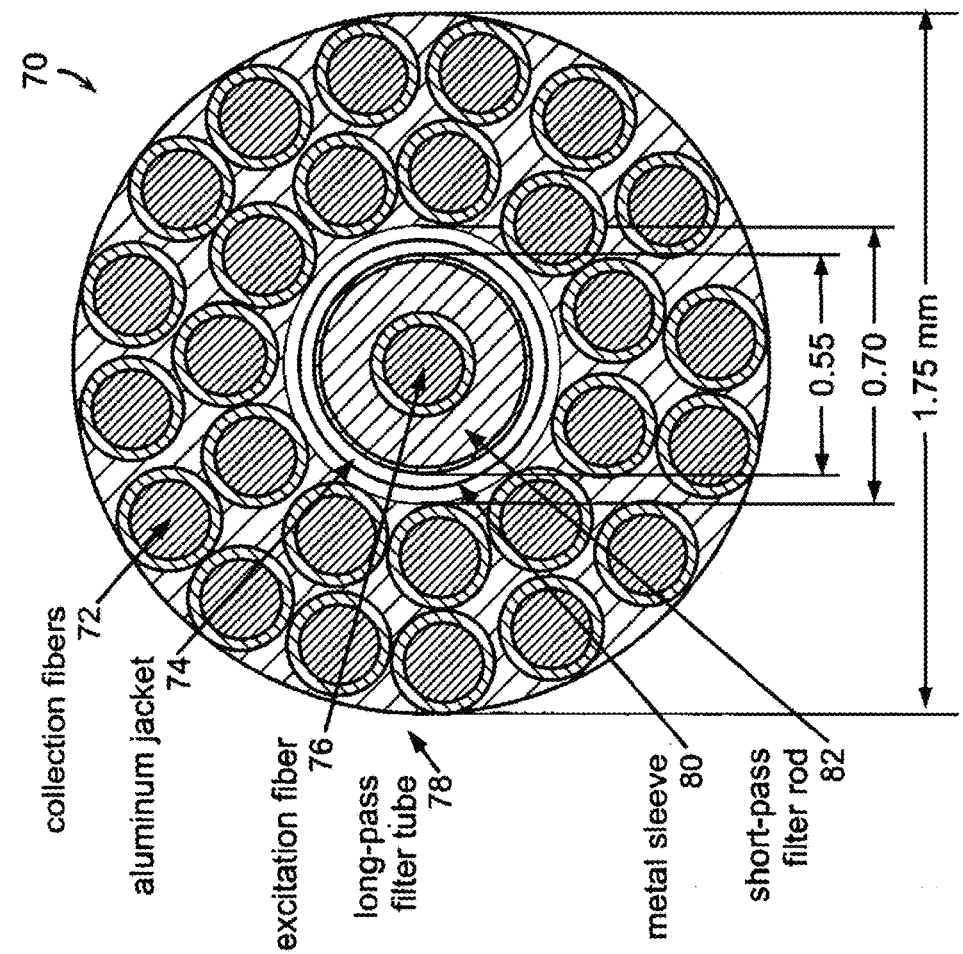
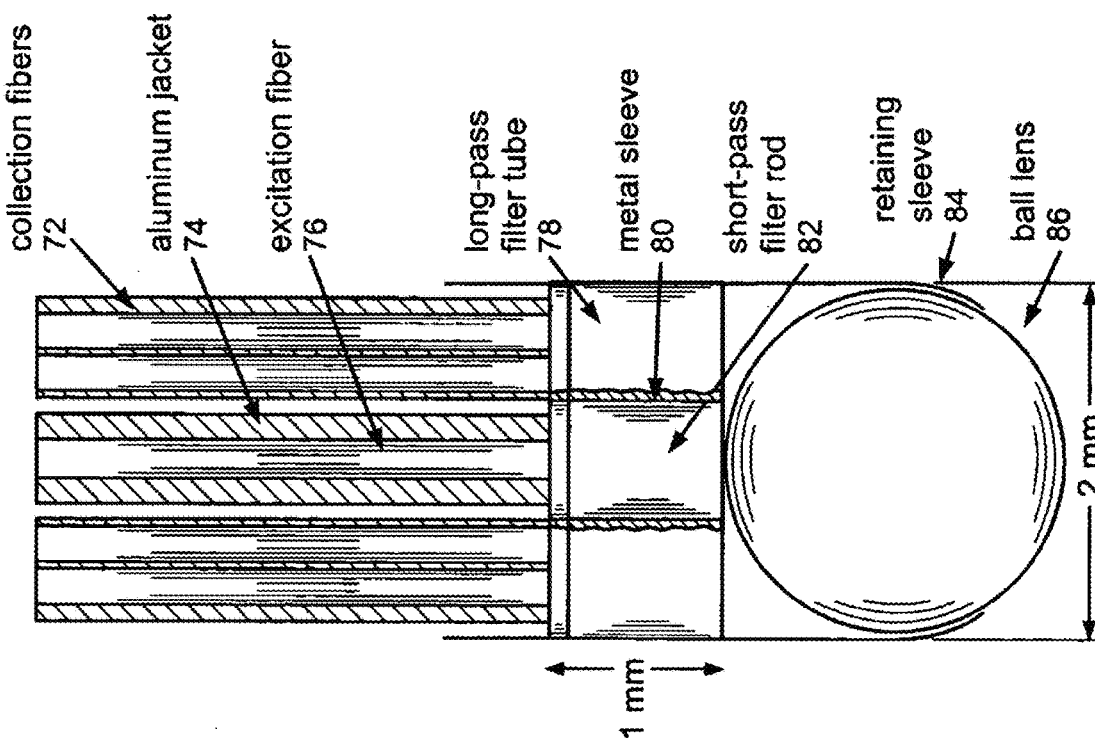
FIG. 10B
FIG. 10A

SYSTEMS AND METHODS FOR DIAGNOSIS OF MIDDLE EAR CONDITIONS AND DETECTION OF ANALYTES IN THE TYMPANIC MEMBRANE

RELATED APPLICATION

The present application claims priority to United States Provisional Patent Application 62/218,989, filed Sep. 15, 2015, the entire application being incorporated herein by reference.

STATEMENT REGARDING FEDERALLY SPONSORED RESEARCH OR DEVELOPMENT

This invention was made with Government support under Grant No. P41 EB015871 awarded by the National Institutes of Health. The Government has certain rights in the invention.

BACKGROUND OF THE INVENTION

A common problem in otolaryngology is the lack of certainty regarding diagnosis for middle ear conditions resulting in many patients being over-treated for their condition. While pneumatic otoscopy and adjunctive tests offer additional information, white light otoscopy has been the main tool for diagnosis of external auditory canal and middle ear pathologies for over a century.

Despite the high incidence of clinical visits that pertain to middle ear pathologies, the ability to make a rapid and accurate diagnosis of these conditions has not improved considerably. Reliable diagnosis of middle ear conditions remains challenging, and the accuracy of currently available methods is limited. At present, standard ear evaluations include interpretation of the clinical history combined with otologic examinations for visual inspection. Otoscopic examinations rely primarily on white light otoscope reflection utilizing a device that has undergone relatively few modifications since it was first described in the 1860s. White light otoscopy has been routinely used by both primary care physicians and specialists for evaluation of middle ear pathologies ranging from highly proliferative and destructive conditions such as cholesteatomas to acute otitis media (AOM) and tympanic membrane perforations.

Cholesteatomas are expansive and destructive lesions characterized by migration of keratinized hyperproliferative squamous epithelium with a fibrous stroma that can occur in the middle ear and mastoid cavity. Under the invading epithelial layer, ossicular and bony erosion occur with potential complications ranging from otomastoiditis and facial nerve paralysis to intracranial meningitis and perilymphatic fistula. While the underlying pathophysiology remains a subject of much debate, these lesions do not metastasize and are not genetically unstable. Nevertheless, they represent a surgical condition, and resolution of the disease process can only occur after complete externalization or removal of the lesion. The objective of cholesteatoma surgery is to obtain a dry, safe ear. However, this may require multiple surgical procedures that can create significant burdens for those affected by this disease. Consequently, it is imperative to develop new tools that can provide near real-time, reliable and low-cost diagnosis of cholesteatoma and facilitate its complete removal during surgery. It is consequently desirable to enable early and robust detection of a wide variety of ear pathologies while also providing specific molecular insight into the onset and progression of the disease states.

However, classical otoscopic evaluation suffers from observer variability and provides limited insight into a disease's defining biochemistry. Molecular methods obtained using biopsy techniques, in contrast, provide objective biomarkers for diagnoses, may permit disease detection prior to morphologic manifestations and, most importantly, can provide patient stratifications for more effective therapy.

In addition to reliable diagnosis of middle ear conditions, there exists a need to reliably and non-invasively measure levels of analytes within the body fluids of a patient. Such analytes can include, for example, glucose in the blood. Raman spectroscopy has been successfully employed to detect molecular species embedded in complex biological samples due to its inherent selectivity (fingerprinting) and multiplexed capability. Further, since the Raman signal has one-to-one correspondence with concentration of the molecular species, it has potential in terms of quantification of concentration levels in body fluids and tissues. While relatively accurate prediction has been achieved in the past, this success has been limited to a personalized setting because skin tissue varies highly from one person to another and a single set of calibration data cannot be used across multiple patients. The lack of active usage of Raman spectroscopy in clinical and point-of-care settings can be attributed to three primary factors:

1. Interference from unwanted optical signals arising from dermis and epidermis tissues and from tissue turbidity.
2. Measured Raman signals from analytes are detected mostly from the interstitial fluid (ISF) and not from the actual blood as the light sampling volume for wavelengths typically used (including near infrared wavelengths) is quite limited. There is a known physiological lag between ISF glucose and blood glucose and, unfortunately, calibration is only possible using blood glucose. This inconsistency results in inaccuracy in the measurement.
3. Skin tissue is highly variable from one individual to another, which necessitates that measurements are person-specific which further contributes to the complexity of calibration.

Thus, improved methodologies are needed to provide effective, non-invasive access to body tissues and fluids where analyte concentration is to be measured.

SUMMARY OF THE INVENTION

The present invention relates to devices and methods for spectral measurement and imaging of middle ear pathologies. Exploiting endogenous biochemical contrast can provide sufficient information to aid the process of middle ear disease diagnosis such as guidance for excision of cholesteatoma, for example.

Embodiments of the present invention include a multi-wavelength fluorescence-based diagnostic and/or video-rate imaging strategy that combines optical elements and software components to provide an otoscopic device. A further preferred embodiment utilizes Raman spectral measurements to provide diagnostic information. Multimodal illumination and detection techniques employing a combination of fluorescence, reflectance, and Raman measurements can also be used. Preferred embodiments can include an imaging detector to view the ear canal during a procedure and one or more spectral detectors to detect fluorescence spectral data or images, Raman spectral data or images, and reflectance spectral data or images. Preferably, a Raman light source has an excitation wavelength of at least 700 nm A spectrometer with one or more wavelength dispersing elements and one or more detector elements can be used to generate spectral data or spectral images. Additional Raman measurements including resonance Raman, surface enhanced Raman, and graphene enhanced Raman spectral measurements can be used for certain applications.

Preferred embodiments include an otoscope that provides a low-cost, detailed and objective diagnosis of common middle ear pathological conditions. In addition, the otoscope can be used to detect analyte concentrations in blood vessels within the tympanic membrane and concentrations of biological material such as mucin in otitis media and otitis media with effusion (OME). The device can detect congenital cholesteatoma using fluorescence and/or Raman detection or imaging to differentiate this proliferative lesion from uninvolved middle ear tissue based on characteristic reference data. Availability of real-time, wide-field chemical information enables more complete removal of cholesteatoma thus allowing for better hearing preservation and substantially reducing the well-documented risks, costs, and psychological effects of repeated surgical procedures.

An in vivo diagnostic approach enables direct visualization through the tympanic membrane thereby allowing clinicians to determine transtympanic middle ear pathologies. A photonic/endoscopic method uses an otoscope, which achieves an additional functional requirement where an otoendoscope can be used at the time of the surgical procedure.

A preferred diagnostic strategy of the present invention is based on acquisition of autofluorescence data at a plurality of wavelengths that identify and quantify the tissue composition. A multi-wavelength, video-rate fluorescence-based imaging device detects the underlying biochemical changes of middle ear pathology. In some embodiments, the device design uses an existing otoscope architecture as the platform and incorporates optical components as a self-contained, modular ("add-on") feature that can also be implemented in an otoendoscope. An advantage of devices of the present invention is the ability to make concomitant fluorescence measurements and conventional otoscopic evaluation to substantially reduce registration errors that are frequently observed in similar devices. The approach described herein is generally applicable to broad-spectrum evaluation of middle ear pathology and, in particular, evaluation of cholesteatoma. The devices herein provide a novel mechanism to acquire real-time intraoperative images of the tissue epithelium thereby optimizing the value of the initial procedure and reducing the necessity for a revision surgery for residual disease.

Embodiments of the current invention can also be used in the quantification of analytes in body fluids. Proper choice of an optical anatomic site for measurement can obviate the issues limiting diagnostic evaluation. The composition of the tympanic membrane is relatively similar among different patients. In an exemplary embodiment, the present invention can be used for non-invasive analyte detection and quantification directly in blood (that is, not interstitial fluid) at an accessible anatomic site.

BRIEF DESCRIPTION OF THE DRAWINGS

FIGS. 10A and 10B illustrate side and end views, respectively, of a fiber probe for illumination and collection of light in accordance with various embodiments of the present application.

DETAILED DESCRIPTION OF THE INVENTION

Figure 1:
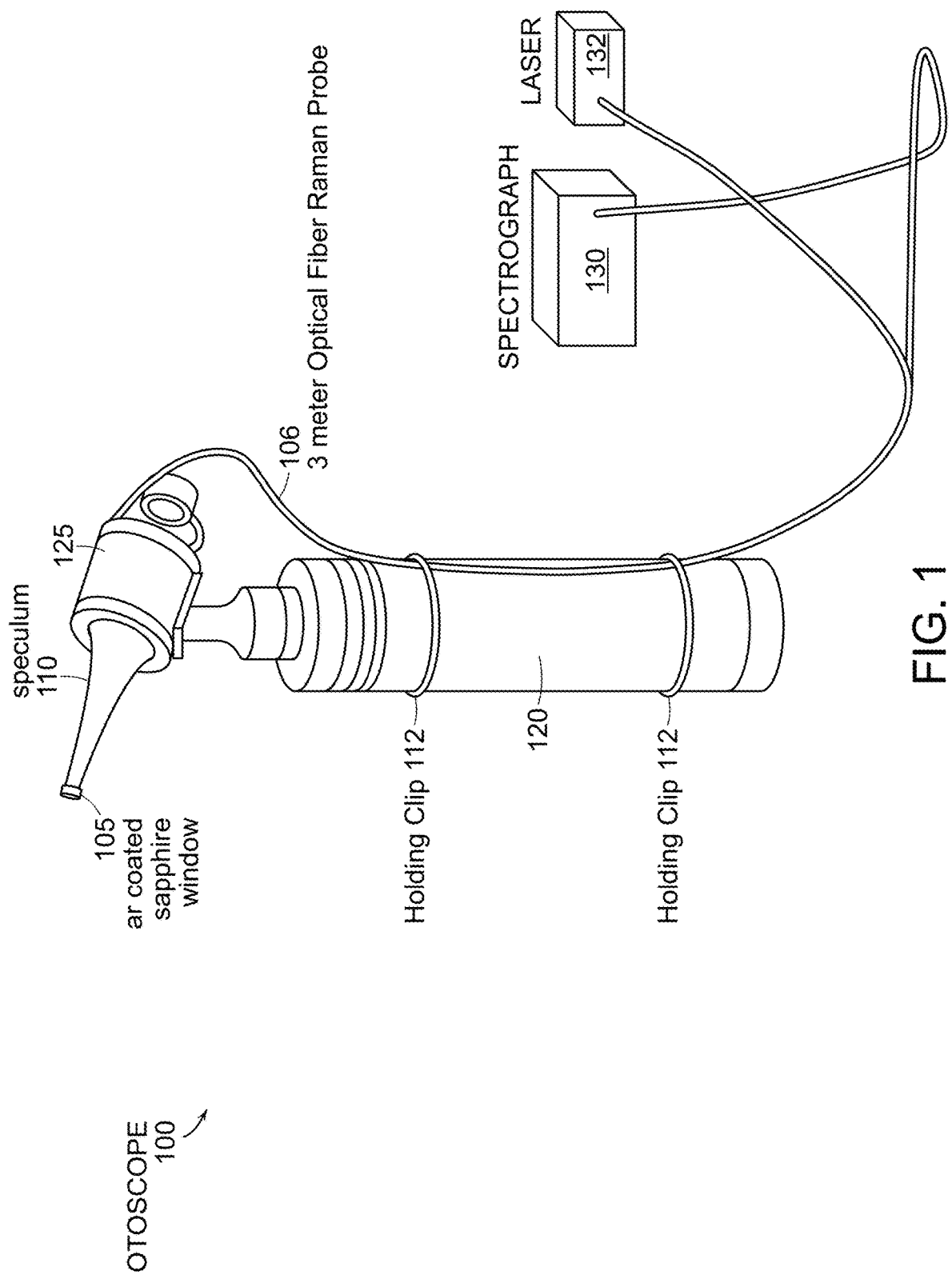
FIG. 1 shows an otoscope according to various embodiments of the present invention.

Standard otoscopic evaluation currently requires subjective visual interpretation of white light reflecting off the tympanic membrane and the middle ear promontory. In other words, the entire process of examining the normal structure, diagnosing diseases, and providing critical input for therapy relies extensively on human recognition of morphologic patterns in vivo. This approach, which is the basis for current decision-making, has been shown to be less than ideal for a number of conditions in particular when it relates to ear examination. More specifically, congenital cholesteatomas tend to be asymptomatic until they reach a significant size, and successful outcomes rely on an astute clinician to make a diagnosis before the lesion causes significant damage to middle ear structures. Detection of congenital cholesteatomas with simple otoscopic examination can be missed altogether or confused with normal conditions such as myringosclerosis. Investigators have opined that even otoscopy with a microscope may not be reliable in predicting the presence or extent of a congenital cholesteatoma.

The inability to biochemically define pathologies is particularly evident in the management of cholesteatoma and myringosclerosis that on gross inspection exhibit nearly identical features. While cholesteatoma is characterized by keratinization of squamous epithelium and aggressive growth of the tissue in the middle ear and mastoid cavity, myringosclerosis is marked by the calcification and hyalinization in the tympanic membrane. The etiology of these pathological conditions (especially myringosclerosis) is poorly understood with limited insights available into the possible association and co-existence of these two conditions. Yet, given the a priori expectation of abnormal tissue, accurate differentiation of these pathologies is as critical as distinction from uninvolved tissue.

From a clinical perspective, two particular issues remain unsolved: 1) the recurrent nature of cholesteatoma due to the difficulty in assuring a clear surgical margin during surgery and 2) the inability to predict which retraction pocket will develop into a cholesteatoma. In this milieu, molecular methods, which provide objective biomarkers for diagnoses, may permit disease detection prior to morphologic manifestations and allow for more sensitive pathological segmentation. Employing non-invasive sensing of the middle ear environment, molecular methods can report not only on the anatomy of the condition but also on its underlying physiology—possibly predicting its future behavior. Multi-colored reflectance, autofluorescence, and molecular-specific Raman methods can be used alone or in combination to improve definition of the underlying biochemistry of these conditions. Embodiments of the present invention provide video-rate, in vivo chemical imaging tools that rely on differential, intrinsic optical signatures between normal and diseased tissues. As such, the present invention represents a measure of objective disease detection and grading that was previously unattainable in clinical practice. Definition of middle ear pathologies in chemical, rather than morphologic, terms has major implications. First, the definition of lesion margins becomes facile and, compared to existing methods, can improve the quality of surgical input. Second, it has been hypothesized that biochemical modifications at the margins are precursors of lesion development and growth. In other words, tissue at the margins of proliferative lesions that appears morphologically benign is reported to be biochemically distinct from uninvolved tissue. Identifying molecular targets from this spatial region, then, can establish new opportunities in detection at early stages and before relapses.

A multi-wavelength spectroscopic otoscope is designed to acquire autofluorescence signals from the middle ear, the tympanic membrane and the transtympanic membrane space. Harnessing multi-wavelength measurements can not only enable the fluorescence-based estimation of multiple endogenous tissue chromophores (prominently collagen, nicotinamide adenine dinucleotide (NADH), elastin, tryptophan, flavin adenine dinucleotide (FAD) and porphyrins) but can also provide the ability to explore differences in tissue absorption and scattering. The latter is of value in understanding the optical penetration depth, which provides a valuable parameter for identification of fluid presence in the diagnosis of acute otitis media (AOM).

Turning to FIG. 1, an otoscope 100 according to various embodiments of the present invention can include a body and a probe. In various embodiments, the body may be a handle or otoscope body 120 having an otoscope head 125, and the probe can be a speculum 110 with a fiber optic assembly attached to the speculum 110. A speculum 110 can be integrated with the body 120 or can be removable and/or replaceable. A cable 106 can include one or more optical fibers and can connect the speculum 100 with a spectrometer spectrograph 130 and/or an excitation source 132 such as a laser. Alternatively, the cable 106 can connect a power source to the speculum 110 to power a source of illumination housed within or near the speculum 110. In some embodiments, the cable 106 is held in position by clips 112. The speculum 110 can have a window 105 at a distal end. In some embodiments, the window 105 can be anti-reflection coated or can be made at least in part from sapphire. Otoscopes used in conjunction with preferred embodiments of the invention can employ imaging optics including one or more lenses to couple light entering a distal aperture of a tip element or speculum to an imaging device in a handheld housing such as described in U.S. Pat. No. 7,399,275, the entire contents of which is incorporated herein by reference. Further preferred embodiments can include optical components for imaging such as those described in U.S. Pat. No. 8,066,634, the entire contents of which is incorporated herein by reference. The distal end of the otoscope can have a diameter in a range of 4-10 mm with a circular distal aperture within a range of 4.2 mm-8 mm. The diameter of the distal tip increases from the distal end to a maximum circumference to provide a curved surface for smooth insertion into the ear canal.

In accordance with various embodiments, a speculum 110 of a multi-wavelength spectroscopic endoscope can be compatible with existing otoscope heads. For example, the otoscope head may be the MacroView™ otoscope head produced by Welch Allyn (Skaneateles Falls, N.Y.). The otoscope head can be chosen to provide greater magnification than a traditional otoscope (for example, up to 30% or more) and may have the ability to adjust focus for variable ear canal length. The otoscope can have a field of view of at least 7 mm at a distance of less than 10 mm from a distal end of the otoscope.

The choice of wavelengths for use with embodiments of the present invention depends upon the chromophores to be measured. For example, wavelengths of 405 nm and 450 nm may be used based on their relative ability to excite certain endogenous tissue chromophores. Specifically, the 405 nm excitation is expected to serve as a principal indicator of collagen as well as the redox ratio, which is defined as the ratio of the FAD fluorescence to the sum of FAD and NADH signals. Previous research suggests a strong correlation between the increase in tissue metabolic activity associated with the progression of epithelial neoplasm and an increase in NADH fluorescence, which corresponds to a decrease in the redox ratio. The 450 nm excitation provides a baseline signal corresponding to the non-specific tissue autofluorescence background (and, presumably, the tail end of some of the aforementioned autofluorescence signals).

The excitation source 132 can reside in a separate enclosure outside the body 120 or speculum 110 or can be mounted on or near the body 120 or speculum 110. The excitation source 132 can include a range of light sources such as a light emitting diode (LED), an array of LEDs, lasers, flashlamps, discharge lamps, or any other suitable source of illumination according to application-specific requirements. Light from the excitation source 132 can be delivered to the speculum 110 through a cable 106.

Figure 2A:
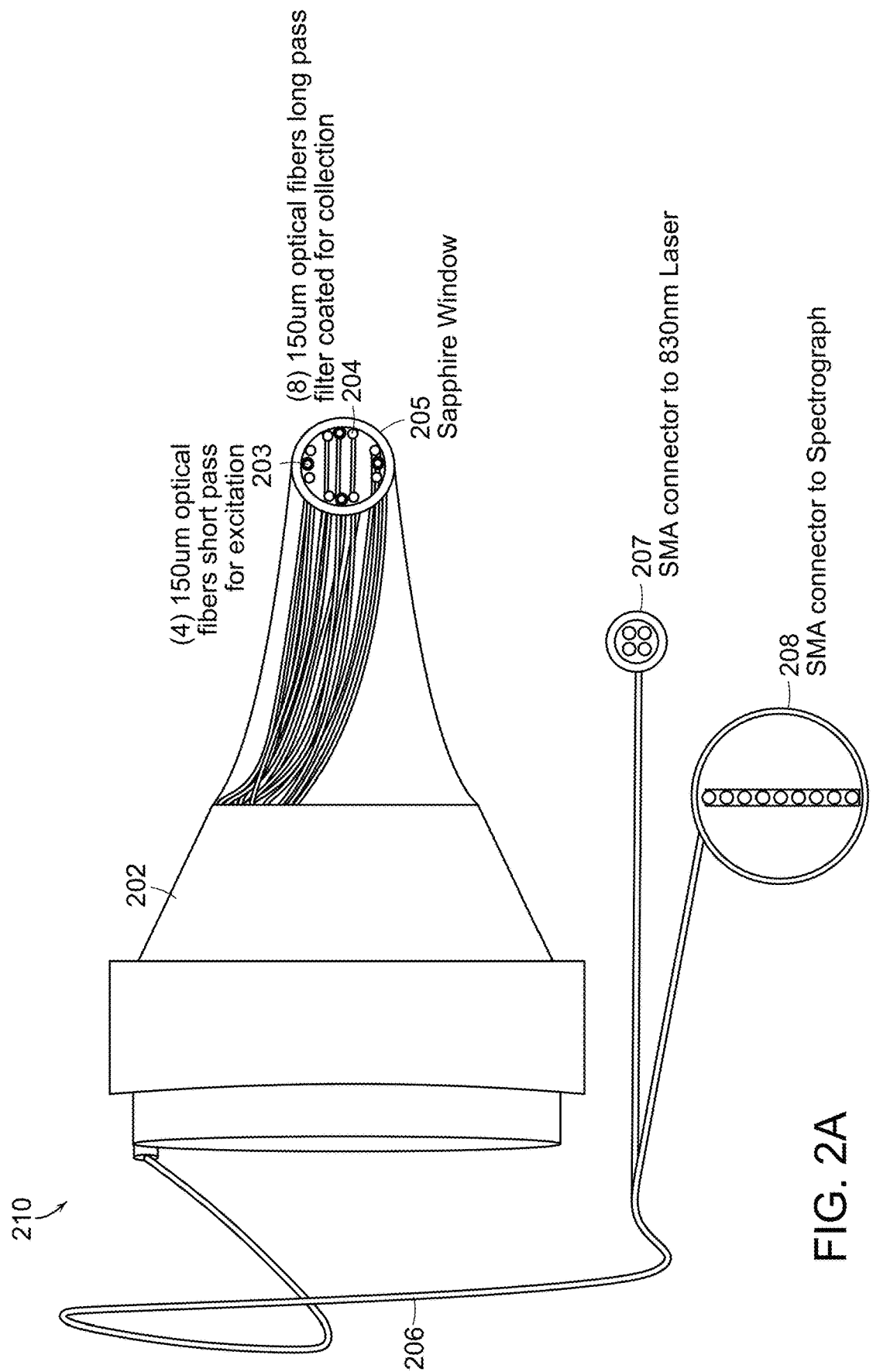
FIGS. 2A and 2B show side and end views, respectively, of a speculum according to various embodiments of the present invention.
Figure 2B:
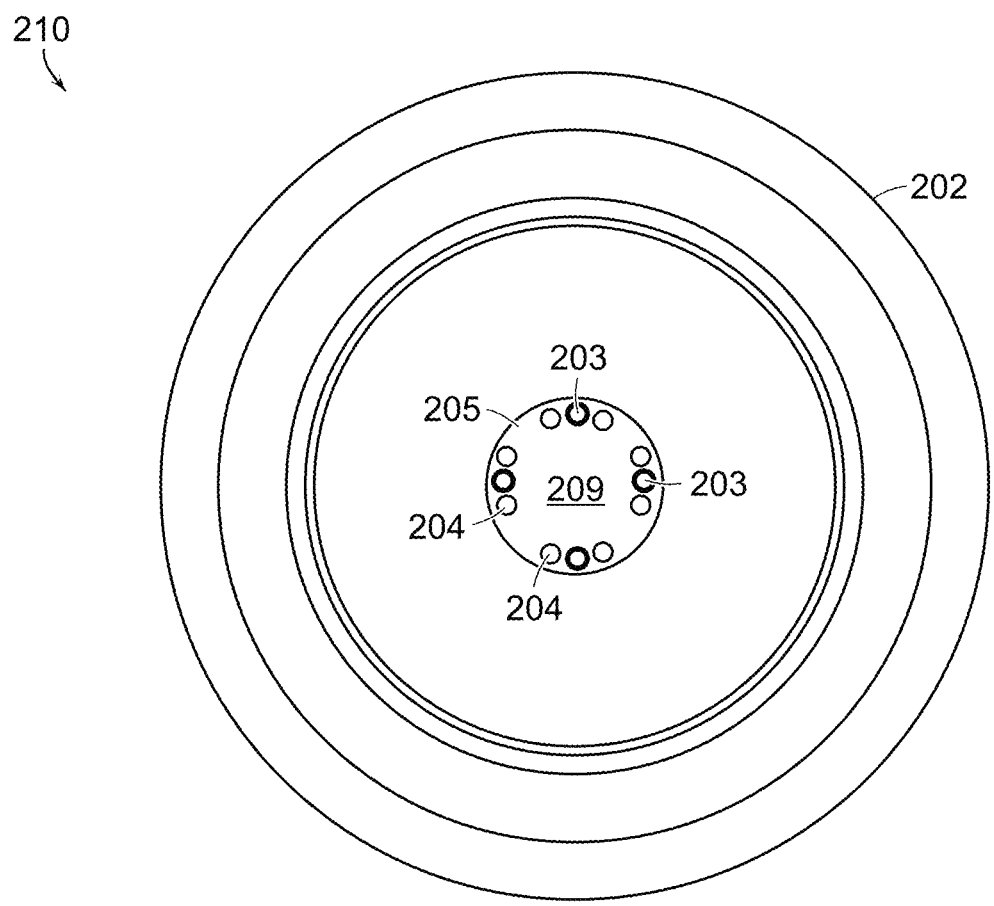

FIGS. 2A and 2B show side and end views of a speculum according to embodiments of the present invention. The speculum 210 may be designed to couple to standard otoscope or endoscope heads or may be designed to be self-contained. In some embodiments, the distal end of the speculum 210 can be operatively sealed by a window 205. The window 205 can be made of sapphire. The speculum 210 can include a speculum body 202. Optical fibers 203, 204 can pass along the interior 209 of the speculum body 202. A cable 206 can connect the speculum 210 to external instrumentation including spectrometers and light sources and may include electrical wires, optical fibers, or both. A proximal end of the cable 206 can be terminated in any suitable manner to facilitate communication with external instrumentation including, but not limited to, SMA connectors 207, 208 of different sizes and shapes. In some embodiments, the distal end of the cable 206 can connect to the optical fibers 203, 204. In some embodiments, optical filters can be included as part of the speculum 201. The optical filters may be placed at a number of locations including, but not limited to, at the distal end of optical fibers 203, 204, between the cable 206 and the optical fibers 203, 204, or at or near the proximal end of the cable 206. The distally mounted filters used for the light delivery fibers 203 and the distally mounted filters used for the light collection fibers provides an embodiment well-suited for a Raman probe. Alternatively, some of the fibers can be used for fluorescence excitation and collection to provide for multimodal operation. In an exemplary embodiment, placement of the optical fibers 203, 204 allows for standard white light imaging through the interior 209 of the speculum 210 using an otoscope.

Figure 3:
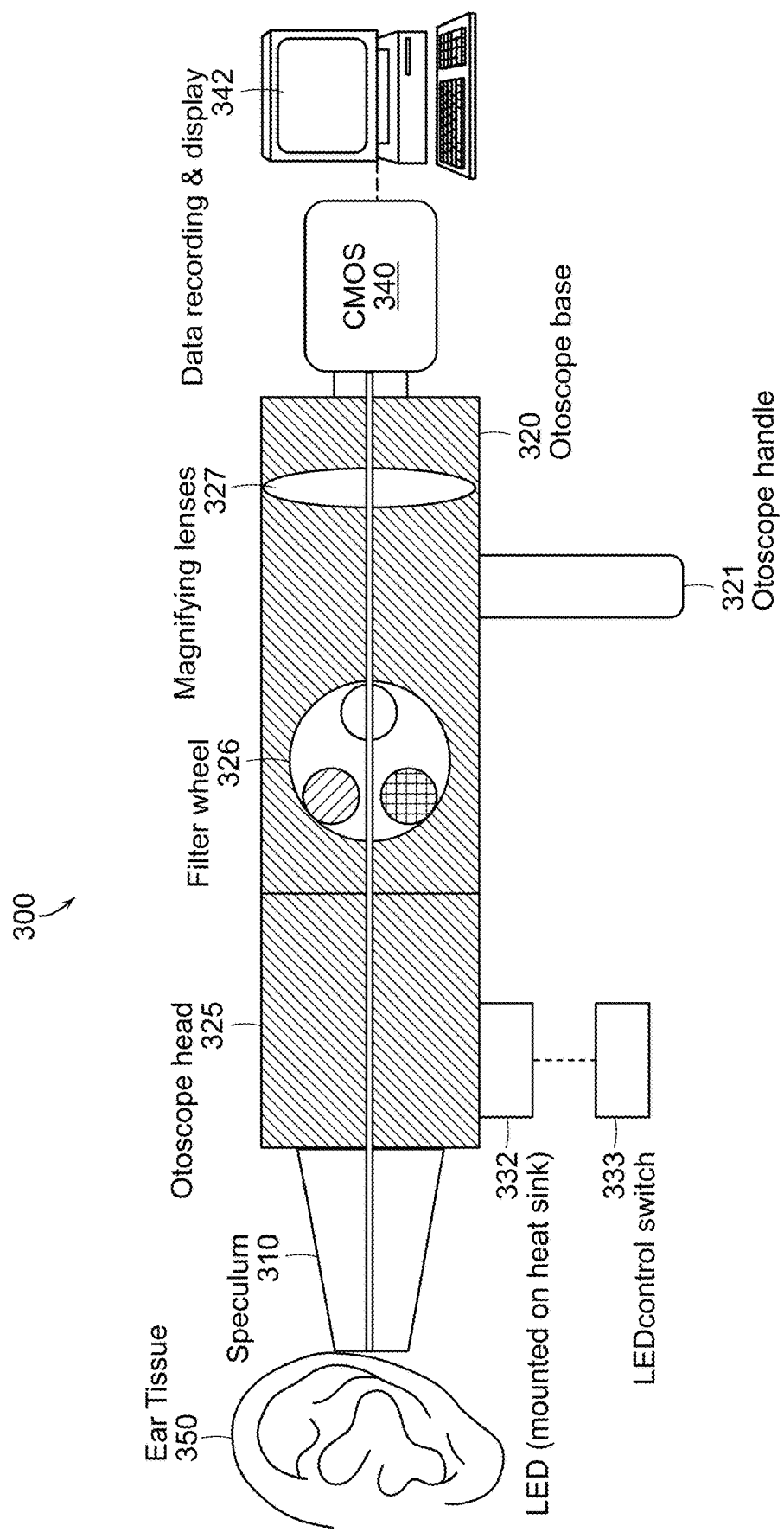
FIG. 3 shows a schematic of an otoscope according to various embodiments of the present invention.

FIG. 3 shows a schematic of an otoscope or otoendoscope 300 according to various embodiments of the present invention. The otoscope 300 can include a speculum 310, an otoscope body 320, and an otoscope head 325. Magnifying lenses 327 and an optical filter wheel 326 can be present within the otoscope body 320. The speculum 310 can be sized to comfortably fit into a patient's ear 350. In some embodiments, the otoscope body 320 is attached to a handle 321 for easier manipulation by a user. The otoscope body 320 may be coupled to a camera 340 that can capture images for recording or display by a computer 342. An excitation source 332 provides illumination for the otoscope.

The excitation source 332 can include one or more high-power light emitting diodes (LEDs) centered at wavelengths ranging from the infrared (IR) through the visible and ultraviolet (UV). An exemplary visible LED excitation source 332 can include four LEDs of different colors, i.e., red (625 nm), green (523 nm), blue (450 nm), and white. The LEDs of the excitation source 332 can be operated individually and independently. The excitation source 332 can include a UV (400-405 nm) LED source having a single LED. The LEDs can be mounted on individual heat sinks that are designed to hold LEDs in a stable enclosure using a spring locking mechanism for maximum efficiency. The heat sinks can be located on the underside of the otoscope head 325. Light from the heat sink cavity can be directed into the ear through the otoscope head 325 and speculum 310. The excitation source can be controlled in some embodiments using a control switch 333. The control switch 333 may be a manual or mechanical pull switch or may be an electric switch that can be controlled by a computer 342.

In some embodiments, light emitted by the excitation source 332 passes through emission filters mounted on a custom-built filter wheel 326. The filter wheel 326 can be secured into the otoscope base 320 using an aluminum optical insert. In some embodiments, the filter wheel can include three 1" diameter filter slots. If a single filter compartment is left empty, traditional white light otoscopic evaluation can be performed. Each specific excitation-emission modality may be swapped into the detection module serially. For example, a 425 nm long pass filter can be employed for 405 nm excitation while a 500 nm long pass filter can be used in conjunction with a 450 nm LED source. The camera 340 can acquire bright field and fluorescence images, and the images can be recorded and displayed by the computer 342. In some embodiments, the camera 340 can obtain single-shot images or videos at up to 25 frames per second.

Measurements have been conducted with human subjects at the Connecticut Children's Medical Center with a fluorescence imaging device in accordance with the invention. Inclusion was limited to patients undergoing an otologic surgical procedure under general anesthesia. Measurements on the ears of 11 patients suffering from cholesteatoma (3: congenital; 8: acquired) were performed with their contralateral normal ears as controls. Additionally, several healthy human subjects were measured for potential variations from the normal controls.

Figure 4:
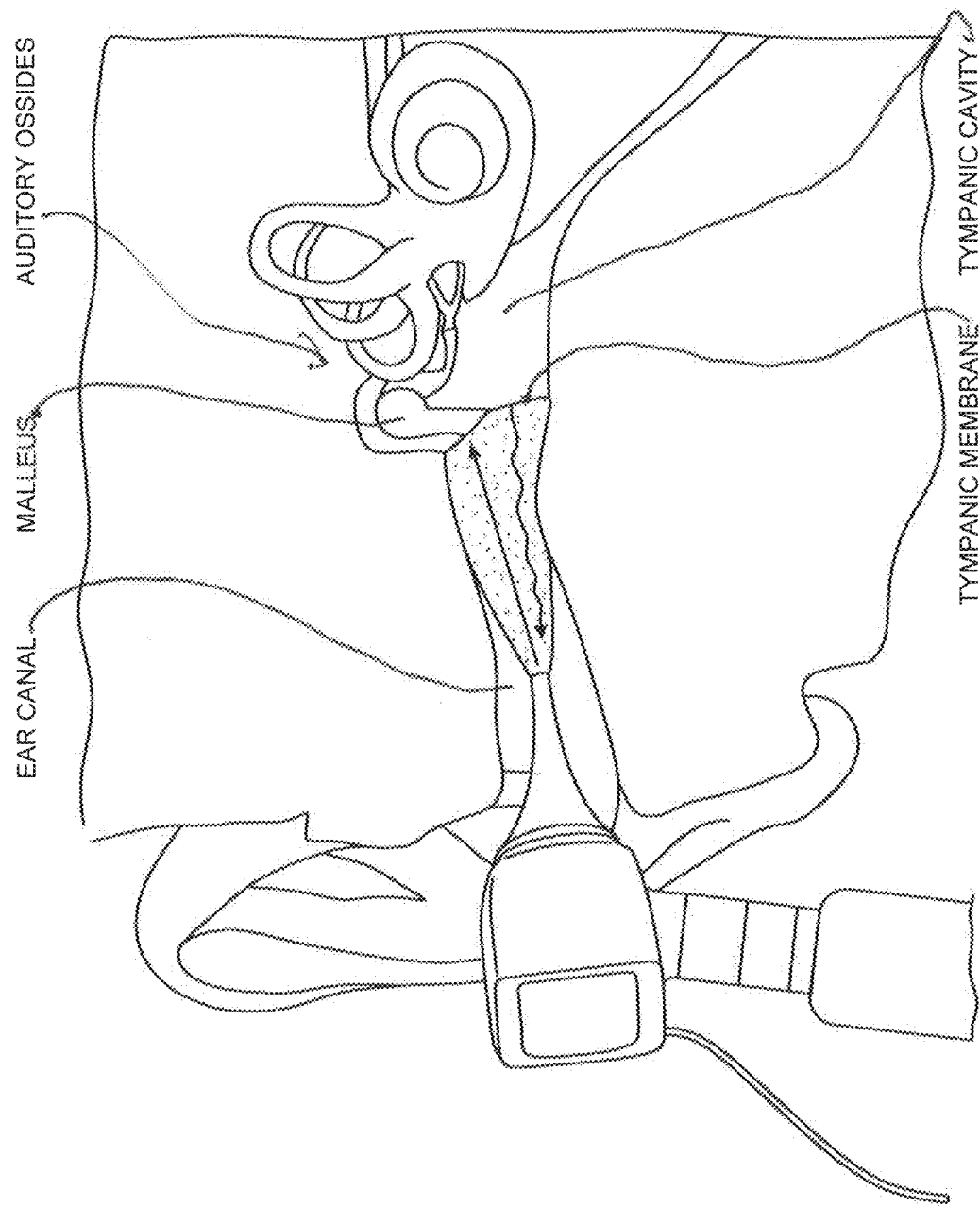
FIG. 4 illustrates a probe according to some embodiments of the present invention is positioned for a procedure.
Figure 5C:
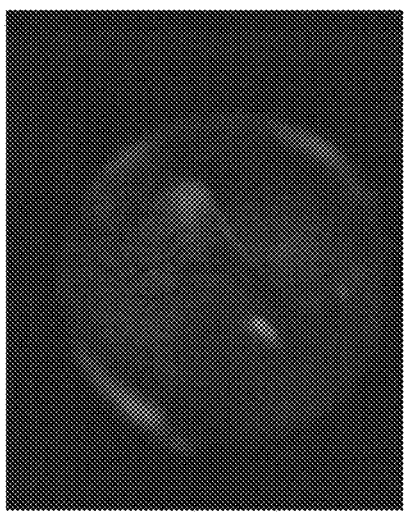
FIGS. 5A-5F show imaging results obtained by an otoscope according to the present invention for a normal ear.
Figure 5B:
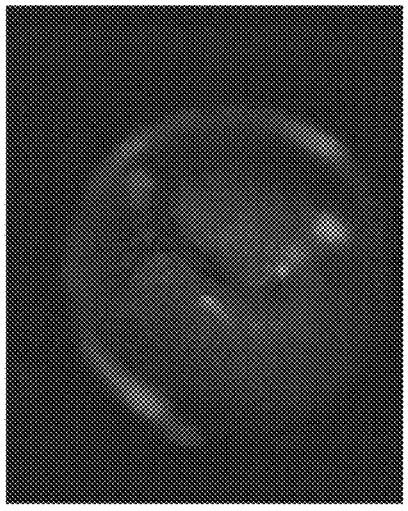
Figure 5A:
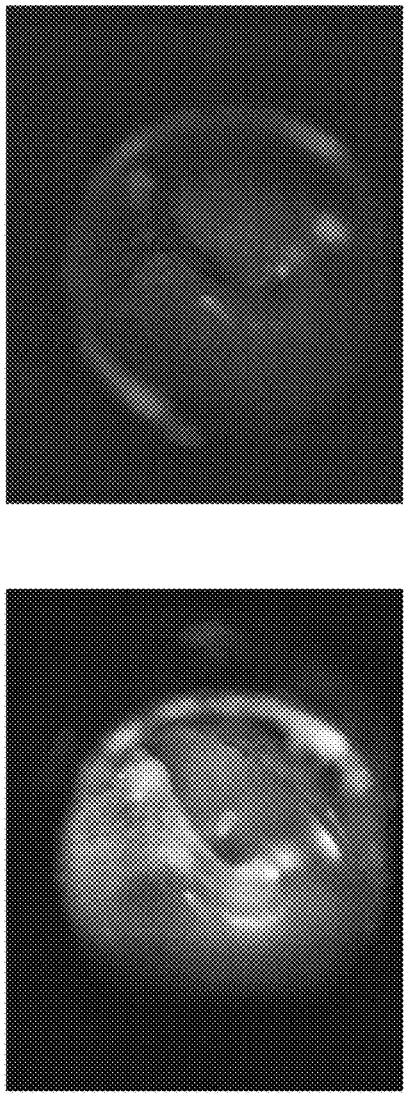
Figure 5F:
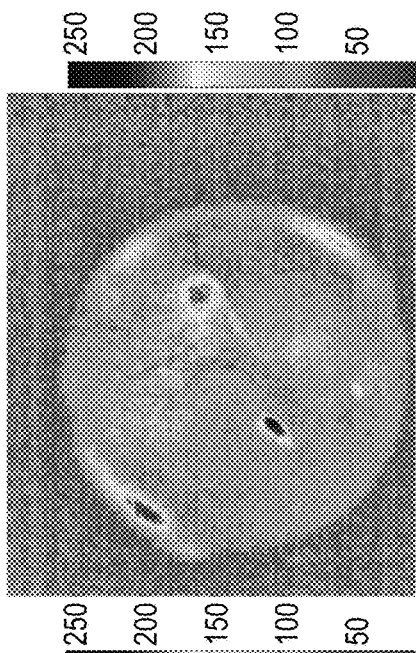
Figure 5E:
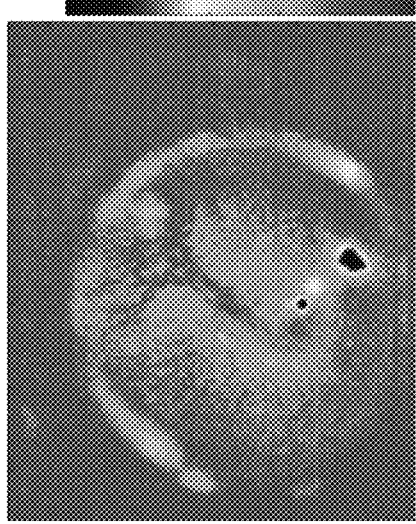
Figure 5D:
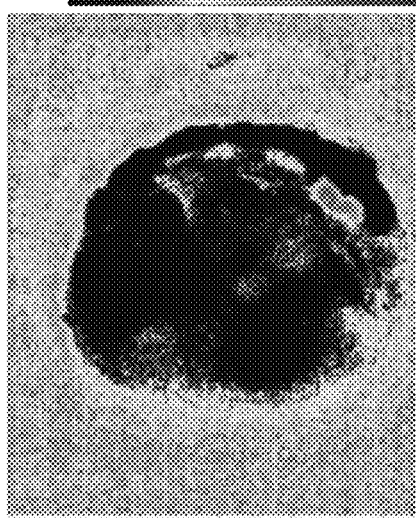
Figure 6C:
FIGS. 6A-6F show imaging results obtained by an otoscope according to the present invention for a diseased ear.
Figure 6B:
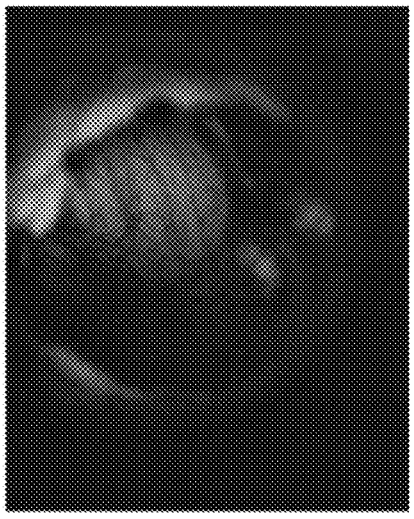
Figure 6A:
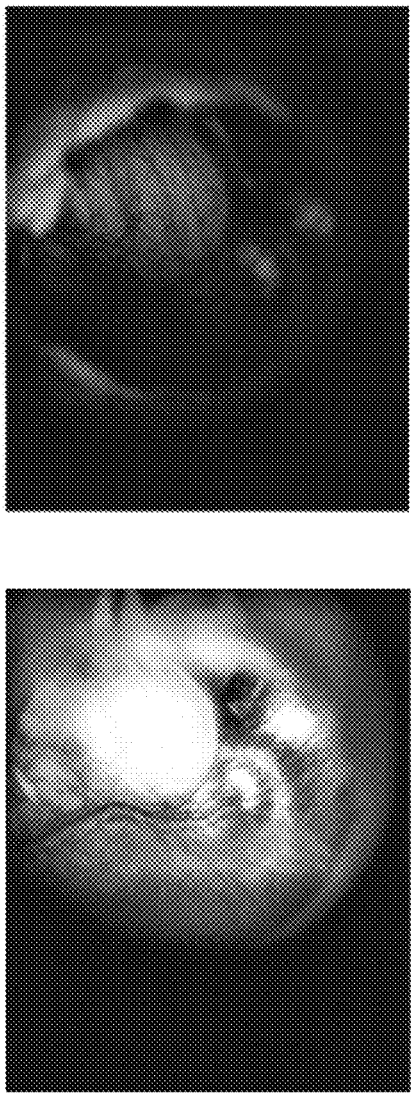
Figure 6F:
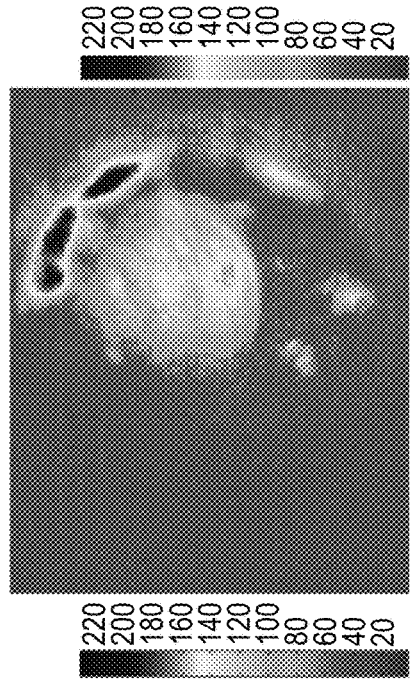
Figure 6E:
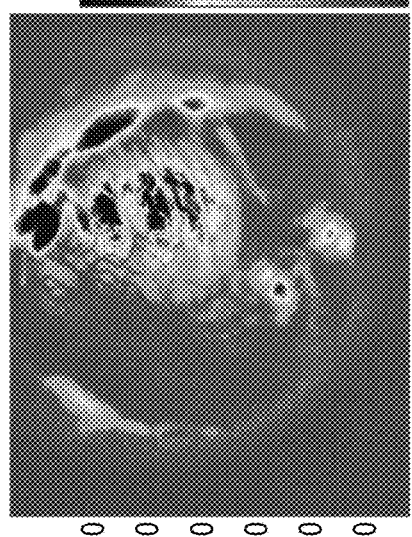
Figure 6D:
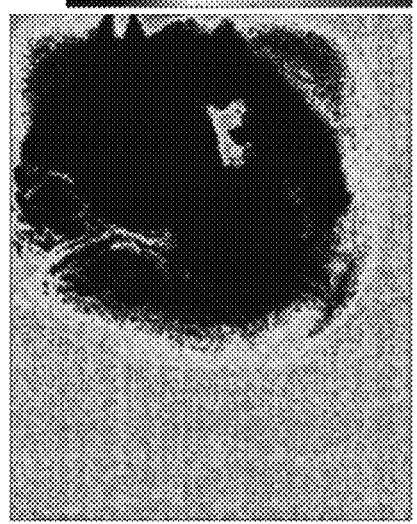

FIG. 4 shows a schematic illustration of the use of an otoscope according to certain embodiments to assess the middle ear of a patient. After initial visual inspection, any impeding cerumen or debris were removed to provide an optimal view of the tympanic membrane. A video otoscope using a 2.5 mm or 4 mm speculum was inserted into the external auditory canal until the tympanic membrane was adequately identified under standard white light inspection. Once adequate identification of the normal anatomic landmarks of the tympanic membrane and middle ear was established, fluorescence image acquisition was initiated. Behind the tympanic membrane, the auditory ossides, including the Malleus, the Incus and the Stapes are located adjacent the tympanic cavity. The 405 nm excitation source was first used to acquire fluorescence images using the 425 nm long pass filter. Subsequently, the 450 nm excitation source was employed to acquire the fluorescence image (with a 500 nm emission filter). The digital images were saved in bitmap (bmp) format and videos were stored in avi format. Image acquisition was performed for both normal ears and ears containing congenital cholesteatomas. The relevant clinical information (pathophysiological condition and spectral dataset) with donor information removed was submitted for analysis and interpretation. Spatial intensity maps and contrast enhancement were pursued in the MATLAB® 8.3 environment (The MathWorks Inc., Natick, Mass.). In addition, contrast enhancement of the color images was done by transforming the image to a color space that has image intensity as one of its components. Singular value decomposition (SVD)-based denoising was performed in conjunction with Contrast Limited Adaptive Histogram Equalization (CLAHE) operation.

Following identification and image acquisition, the cholesteatoma samples were surgically removed and sent for histological processing. Specifically, the samples were fixed in 10% neutral buffered formalin and were embedded in paraffin. Sections were subsequently cut for hematoxylin and eosin (H&E) staining prior to microscopic examination by a board-certified pathologist.

White light illumination was employed to adequately identify the anatomic landmarks in the middle ear as per the standard operating procedure of a clinical examination. This step allows for adequate detailing of the tympanic membrane anatomy and vasculature. Additionally, white light illumination also offers adequate transtympanic illumination of the promontory in the middle ear, which is visible due to the translucent nature of the tympanic membrane.

Otoscopic evaluation of a normal ear involves a variety of structures with different tissue types from external auditory canal skin to the thin translucent tympanic membrane to highly reflective bony ossicles and promontory. The various structures of the middle ear and mastoid have different histological compositions and different concentrations of endogenous fluorophores. All of these structural variations give specific optical properties that can be potentially targeted using different excitation wavelengths of light.

FIGS. 5A-5F show representative images of normal tympanic membrane and middle ear obtained using (A) standard white light otoscopy and fluorescence imaging with (B) 405 nm and (C) 450 nm excitation, respectively. It is evident that the overall intensity of the white light image is (expectedly) much higher than that obtained from autofluorescence. The obtained intensity patterns were quantified and plotted following adaptive contrast enhancement (FIGS. 5 (D)-(F)) in order to better highlight features and the margins of the lesion. To obtain the bottom row of figures, contrast-limited adaptive histogram equalization (CLAHE) was performed in MATLAB®. In contrast to conventional histogram equalization, this algorithm operates on small data regions (tiles) rather than the entire image. Each tile's contrast is enhanced so that the histogram of each output region approximately matches the specified histogram.

The white light image exhibits the cone of light phenomenon that is commonly observed during examination of the tympanic membrane with an otoscope. This phenomenon is simply a light reflex event wherein shining light on the tympanic membrane causes a cone-shaped reflection of light to form in the anterior inferior quadrant. Distortions of the cone of light are often used as a marker for increased inner ear pressure. On the other hand, fluorescence imaging with 405 nm excitation and 425 nm emission filters shows that there is no observable signal from the tympanic membrane. However, evidence of fluorescence from the lateral process of the malleus and faint fluorescence from the bony promontory is present. Significant hemoglobin-based absorption is also noticeable, especially in the malleus. Such absorption provides an additional diagnostic marker but also complicates quantification of the intrinsic fluorescence signal and, therefore, extraction of direct biochemical information about the identity and concentration of the tissue fluorophores. Autofluorescence in the lateral process of the malleus and promontory is also seen using 450 nm excitation. There was also evidence of a strong fluorescence signal from cerumen in the external auditory canal at both excitation wavelengths.

The congenital cholesteatomas are defined as epithelial inclusions behind an intact tympanic membrane in a patient without history of otitis media. FIGS. 6A-6F display a white light image (A) and fluorescence images with (B) 405 nm and (C) 450 nm excitation acquired from a representative congenital cholesteatoma in vivo. The white light image shows the clear presence of a cholesteatoma in the posterosuperior aspect with increased vascularity of the tympanic membrane. Importantly, the cholesteatoma shows a broad fluorescence pattern with evidence of auto-fluorescence at both 405 nm and 450 nm excitation. Furthermore, in both the fluorescence images, there is little or no interference from the autofluorescence emitted by the bony promontory, and there is a complete absence of autofluorescence from the tympanic membrane. Thus, the fluorescence images provide clear differentiation between the cholesteatoma and the surrounding uninvolved mucosa. The presence of the cholesteatoma is also unambiguous in the bright field image due to its highly reflective nature stemming from the large keratin content; however, the presence of the blood vessels and, critically, the boundaries of the lesion are better defined in the autofluorescence images.

Figure 7:
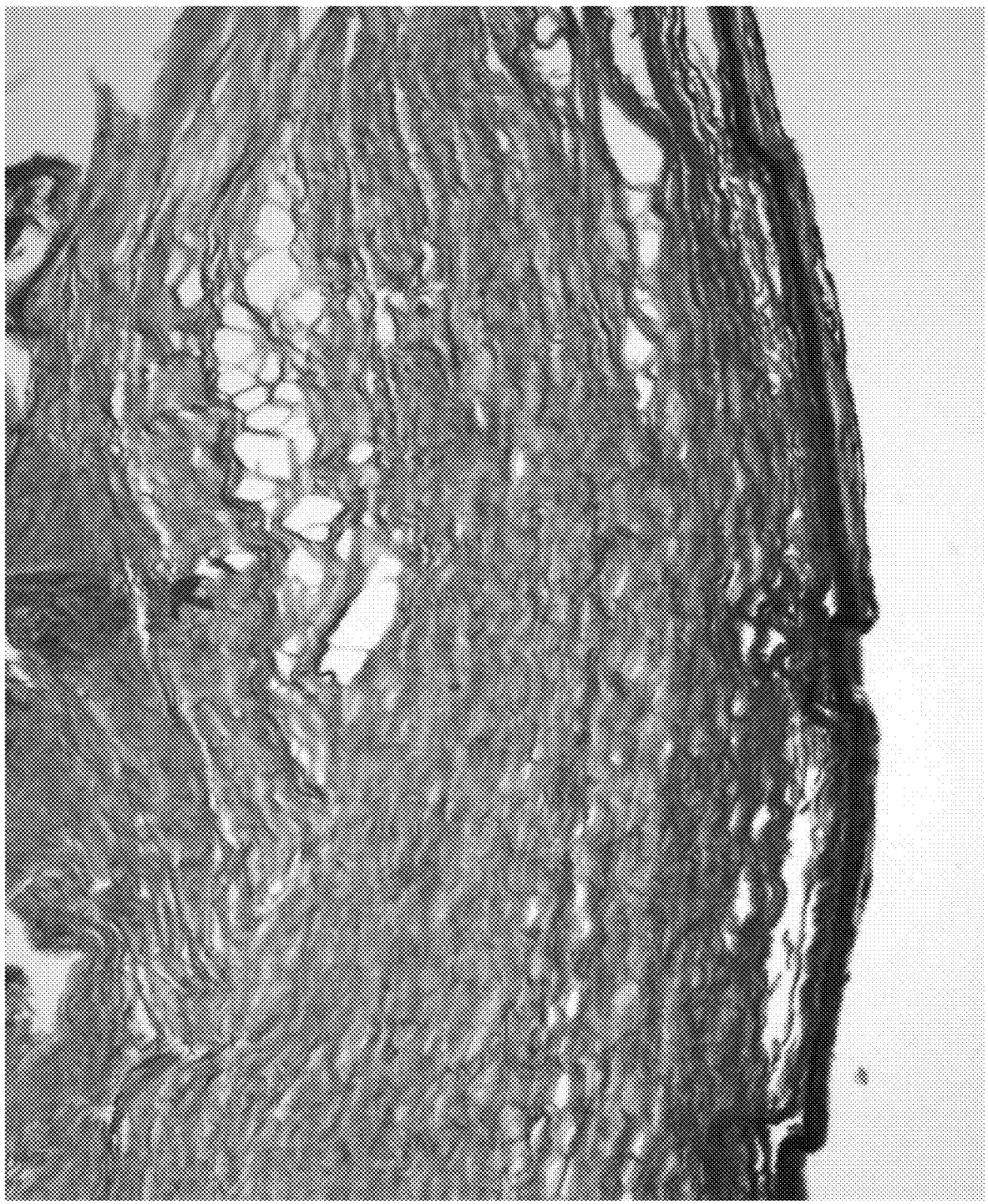
FIG. 7 shows a hematoxylin and eosin (H & E) image of a portion of diseased ear tissue in accordance with the present invention.

Measurements indicate the presence of substantive autofluorescence at the two different wavelengths in cholesteatoma. These two signals can arise from the contribution of multiple fluorophores to the overall signal levels. The peak fluorescence emission for keratin at 382 nm with a 50 nm full width at half-maximum has an excitation at 277 nm. Thus, the fluorescence signals acquired here reflect the tail end of the keratin signal with the 405 nm excitation image displaying a substantially larger component of the keratin contribution compared to the 450 nm excitation image. Furthermore, strong keratin fluorescence from the keratinized epithelial layer exhibits similar excitation and emission characteristics to those of collagen. Such a signal can overwhelm the assessment of NADH/FAD fluorescence in the epithelium and collagen fluorescence in stroma because the former has optimum excitation in the same wavelength region. This overlap can necessitate the application of multivariate calibration techniques to unscramble the specific contributions in a spectral dataset. FIG. 7 shows the H&E stained histologic image of the cholesteatoma, which illustrates the presence and abundance of keratin in this class of hyperproliferative lesions.

The data indicate that the different chemical composition of tissues in the tympanic membrane and middle ear provides important information that is useful in differentiating a cholesteatoma from normal mucosa at the point of care. The ability to demarcate the margins is attributed to: (a) the high keratin content present in cholesteatoma; and (b) the metabolic activity in the hyper-proliferative lesion. Cholesteatomas have shown a higher apoptotic rate when compared to other external canal cells. This indicates why cholesteatomas are metabolically more active than the normal tympanic membrane and external auditory canal tissue resulting in significant NADH/FAD-based autofluorescence. Evidently, determining measurable chemical and metabolic differences between normal and pathologic ear conditions (including inflammatory processes) can help in the development of better diagnostic instrumentation to improve earlier detection and considerably reduce the number of recurrences following surgery. More wavelengths and narrow-band optical filters can improve diagnostic algorithms to better identify these conditions. Also, time-resolved fluorescence measurements can provide vital clues in extricating the precise source of the fluorescence signals as the NADH/FAD and collagen fluorescence exhibit substantively different time-decay processes.

Additionally, pathologic changes in proliferative lesions in the middle ear such as cholesteatoma require increased vascularization of the surrounding perimatrix to sustain growth. This increase in vascularity is evident due to the ability of hemoglobin to absorb light in the blue-green region of the visible spectrum. Also observed was significant fluorescence in cerumen most likely due to the high keratin concentration. Finally, although there was no actual autofluorescence emitted from the tympanic membrane, the translucency of the membrane allowed fluorescence from the promontory to be captured. These properties can be altered in cases of severe inflammation and are of value in detection of other pathologies such as AOM.

The non-perturbing nature of this imaging approach is attractive in conducting otoscopic examination as is the capability to provide information without the use of contrast agents, which may be ototoxic. This imaging modality can be readily adapted to oto-endoscopes, which are currently used in otologic surgery to reach difficult to access areas intra-operatively.

The present invention demonstrates the ability to provide relevant chemical images that map the spatial distribution of important constituents such as collagen, NADH, FAD and keratin. Aside from congenital cholesteatoma detection, embodiments hereof have shown that spectroscopic otoscopes of the present invention can provide additional information on proliferative lesions and especially in highlighting contours and vascularity. These measurements show the feasibility of applying the approach for direct in vivo imaging of cholesteatomas in order to aid surgical removal of the lesion thereby reducing the likelihood of residual disease and improving surgical outcomes and patient prognosis. In fact, the presence of residual lesion (which has been reported to be as high as 30%) is widely attributed to be a primary driver of cholesteatoma recidivism. See Valdez, Tulio A. et al., "Multiwavelength Fluorescence Otoscope for Video-Rate Chemical Imaging of Middle Ear Pathology," Analytical Chemistry, 86, 10454-10460 (2014), the entire contents of which is incorporated herein by reference.

In some embodiments, the system can be configured to maximize throughput including installation of cameras with high quantum efficiency in the UV-visible region. In some embodiments, the signal-to-noise ratio of the system can be improved by the application of denoising algorithms. For example, wavelet-based denoising algorithms have been employed with varying degrees of success by transforming the data in a manner where only a few large (and therefore meaningful) coefficients are retained with the noise being removed by eliminating the smaller wavelet coefficients. A large number of excitation-emission wavelength combinations can be used to accurately discern normal middle ear mucosa from cholesteatoma.

In accordance with various embodiments, the device can acquire spatial-spectral data cubes where a spectrum is obtained at each uniquely defined spatial point (x, y). Elucidation of the identities and content of the chromophores and/or scatterers at each spatial point can enable true molecular imaging. Multivariate curve resolution of the hyperspectral datasets can provide the spatial distributions of biochemical markers that indicate changes in pathophysiological functions. In various embodiments, fluorescence lifetime imaging can be used for otoscopic examination as it provides an additional dimension of information missing in time-integrated steady-state measurements and is sensitive to the biochemical microenvironment. In contrast to direct intensity measurements, fluorescence lifetimes are unaffected by variations in excitation intensity and sources of optical loss and thus offer a route to quantification for in vivo measurements. The interpretation of autofluorescence signals can be confounded by a multilayered tissue structure as the acquired images represent the volume-averaged contributions of the fluorophores from different tissue layers. In some embodiments, a depth-resolved technique such as confocal fluorescence imaging is used to provide a more accurate understanding of the layer-specific fluorescence signals while also avoiding non-analyte-specific absorption and scattering effects.

Additional devices and methods for spectroscopic measurements can utilize analytical methods described in Spegazzini, Nicholas et al., "Spectroscopic approach for dynamic bioanalyte tracking with minimal concentration information", Scientific Reports, 4:7013, DOI:10.1038 (Nov. 12, 2014), the entire contents of which is incorporated herein by reference.

In addition to cholesteatoma, other routinely encountered diagnoses, especially acute otitis media (AOM), can be probed using devices and methods according to the present invention. AOM represents the most common affliction necessitating medical therapy for children younger than 5 years in the USA and has a significant impact on the health of children and on the cost of providing care. The proposed devices and methods are sensitive to fluid accumulation, which is a hallmark of AOM. Because most diagnoses made today are of moderate grades with physicians prescribing antibiotics even in the presence of significant diagnostic uncertainty, a tool that can robustly segregate AOM subtypes can be of immense value in routine ENT examination, especially for pediatric cases.

In accordance with various embodiments, vibrational spectroscopic methods such as Raman spectroscopy can be used for diagnosis of precancerous lesions and cancers in a number of organ systems. By combining the chemical specificity of Raman spectroscopy with wide-field fluorescence imaging, a multidimensional algorithm can be used for differentiating a broad range of middle ear pathologies.

In some embodiments, the devices and methods of the present invention can provide spectroscopic detection of various bioanalytes including blood glucose from the middle ear vasculature. A further detection method is Raman spectroscopy. While Raman spectroscopy provides a powerful tool for non-invasive, real-time, and multiplexed diagnostics of biological samples due to its exquisite molecular specificity and low sample preparation requirements, the confounding signal from tissue fluorescence and spectral shape alteration due to turbidity has prevented the widespread usage of Raman spectroscopy as a diagnostic tool in clinical and point-of-care settings. When considering non-invasive Raman measurements in human subjects, the preferred anatomic site has a thin layer of epidermis, low pigmentation and a substantially high distribution of blood capillaries. Middle ear vasculature, in general, and the tympanic membrane, in particular, meet the above requirements. By using the tympanic membrane as an anatomic site, devices and methods of the present invention can detect and quantify the bioanalyte concentration from actual blood as opposed to interstitial fluid (ISF), which has typically been used in non-invasive measurements. A Raman system in accordance with various embodiments can be based around a fiber optic probe where the fiber probe is a part of a speculum or a wearable device. In some embodiments, the wearable device can be headphones connected to the probe. Raman devices in accordance with the present invention can utilize fiber optic delivery using distally mounted filters for light delivery and light collection optical fibers as described in detail in connection with U.S. application Ser. No. 10/407,923, filed on Apr. 4, 2003, the entire contents of which is incorporated herein by reference. The Raman diagnostic measurements described herein can be used in conjunction with reflectance, fluorescence and Raman measurements as described in U.S. application Ser. No. 11/492,301, filed Jul. 25, 2006 and also in U.S. application Ser. No. 13/338,920, filed on Dec. 28, 2011, the entire contents of the above applications being incorporated herein by reference.

Further preferred embodiments can include Raman or multimodal instruments utilizing portable mobile devices such as web-enabled wireless communication devices such as cellular phones having data processor(s), memory and control software programmed to execute the measurements described herein. Further details regarding such portable measurements are described in U.S. application Ser. No. 13/167,445, filed Jun. 23, 2011, the entire contents of which is incorporated herein by reference.

Figure 8:
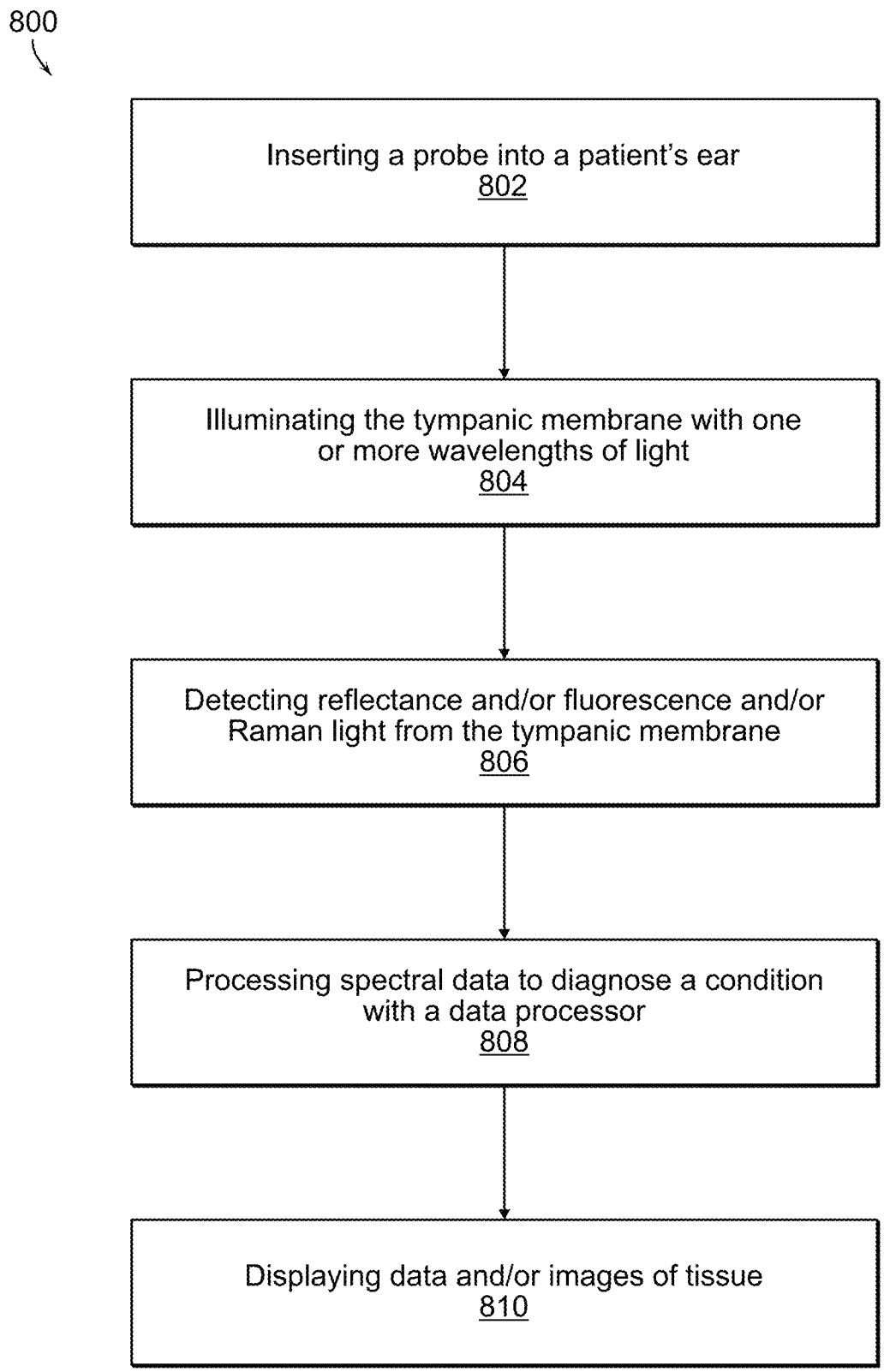
FIG. 8 illustrates a process sequence in accordance with preferred embodiments of the invention.

Devices and methods described herein can be used in the diagnostic process 800 illustrated in FIG. 8 in which a probe is inserted 802 into the ear of a patient, illuminating 804 the tympanic membrane with one or more wavelengths of light, detecting 806 reflectance, fluorescence and/or Raman light, processing 808 spectral data as described herein and displaying 810 the data and/or images for diagnosis and visualization. These measurements can be used to guide surgical procedures or provide periodic measurements of tissues and/or blood analytes.

Figure 9A:
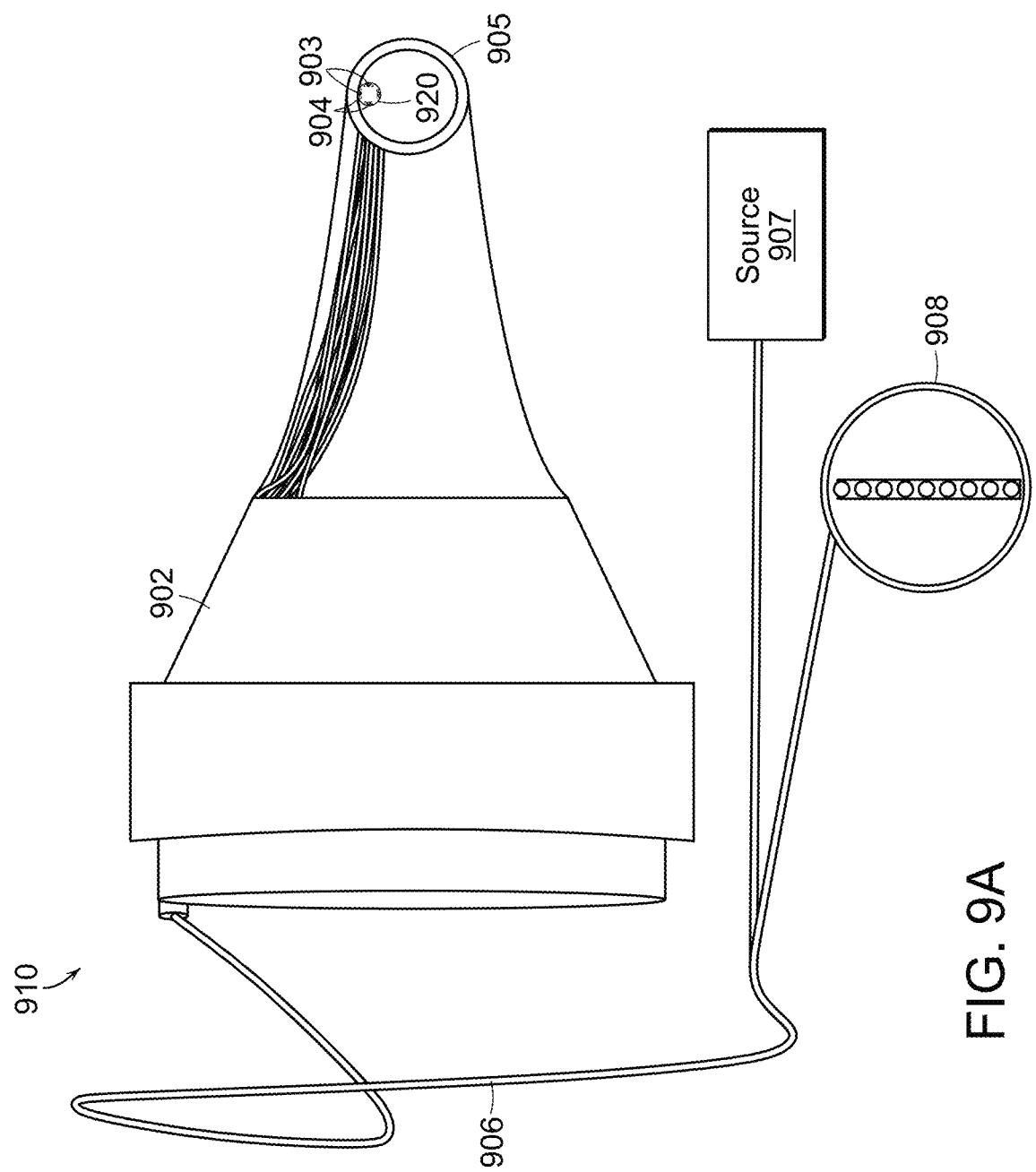
FIGS. 9A and 9B illustrate side and end views, respectively, of a speculum according to various embodiments of the present invention.
Figure 9B:
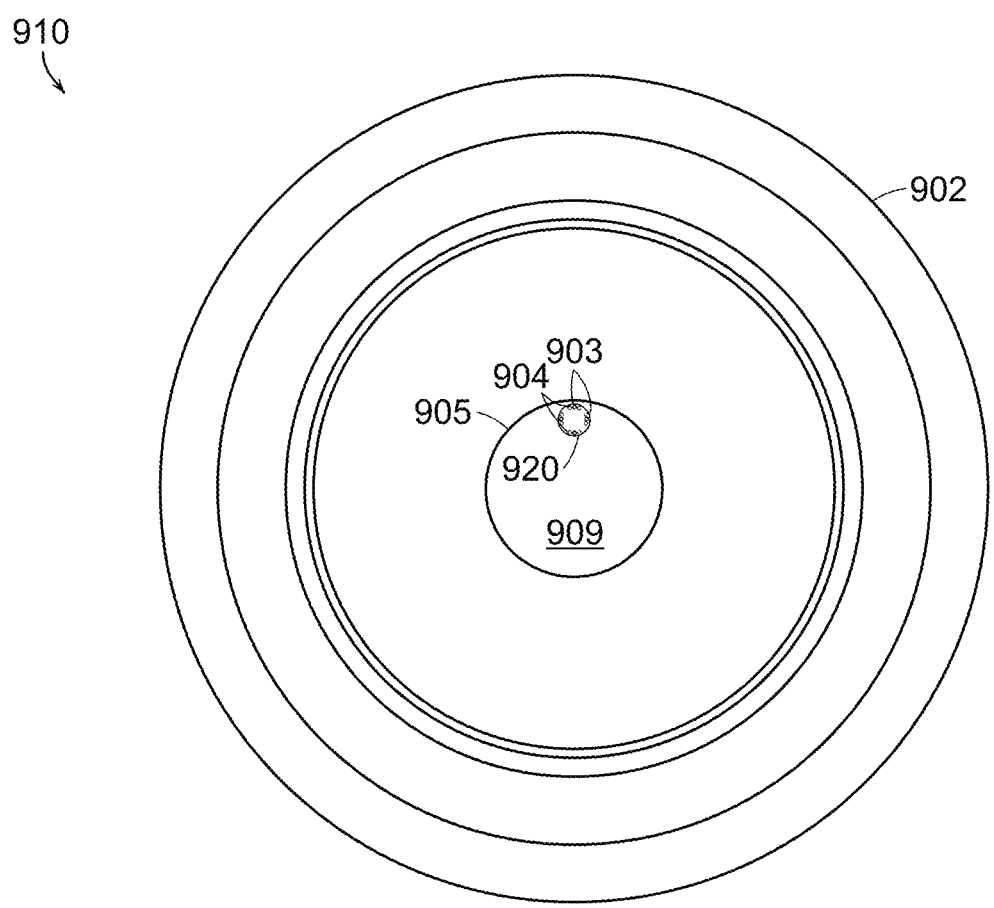

FIGS. 9A and 9B illustrate side and end views of a speculum 910 according to embodiments of the present application. The speculum 910 may be designed to couple to standard otoscope or endoscope heads or may be designed to be self-contained. The speculum 910 can include a fiber probe 920 in some embodiments. The fiber probe 920 can include one or more excitation fibers 903, one or more collection fibers 904, and additional beam-shaping and optical elements.

In various embodiments, the fiber probe 920 can be fixed with respect to a distally placed window 905 of the speculum 910. In other embodiments, the fiber probe 920 can be moved to any position along the perimeter of the window 905 by a user prior to or during a measurement. In an exemplary embodiment, placement of the fiber probe 920 allows for standard white light imaging through the interior 909 of the speculum 910 using an otoscope. In some embodiments, fiber probe 920 can be supported at the center of the window 905 using a strut structure similar to placement of a phase plate in an optical system. In such embodiments, images acquired through the open portions of the window 905 (e.g., white-light images) can undergo post-processing to remove the effects of the obstructive strut structure before presentation to a user for viewing.

FIGS. 10A and 10B show a longitudinal and transverse view, respectively, of the fiber probe in shown in 9A and 9B. The probe 70 can include a two piece multiple-wavelength (for example, dual wavelength) micro-optical dielectric filter module for minimizing and preferably eliminating fiber Raman background in the delivery and collection fibers. This module consists of a rod 82 carrying the excitation dielectric filter coating on one plane face, fitted into the tube 78 carrying the collection dielectric coating on one plane face of the tube. Rods and tubes are used in the embodiment that are made of either sapphire or fused silica which are separately coated with their respective filters prior to assembly. The rod can be wrapped or coated with a thin sheet of metal 80 to provide optical isolation between the components. The module can then be placed at the distal end of the probe between the fiber bundles and a lens system for collimating the light beams having a lens 86 such as, for example, a ball lens. The lens collects light from high angles and a large area effectively overlapping excitation and collection regions. In some embodiments, the ball lens can be fabricated and supplied by Edmund Industrial Optics, New Jersey. In a preferred embodiment, sapphire lenses or windows can be used that are coated with anti-reflection coatings and have an appropriate index for angular acceptance, for example, 1.77. In a preferred embodiment, the filters are deposited on sapphire or quartz rods and tubes for proper registration with fibers.

For the excitation fiber, using a low numerical aperture (NA) fiber is useful although there are issues to contend with. At the input end, the low NA can make coupling the energy into the fiber more difficult. In a preferred embodiment, when exciting with a laser with a low beam divergence, reasonable care in mounting the fiber and the matching optics avoids this problem. At the output end the beam is more confined. This makes the filter construction simpler and more efficient, but illuminating a larger area in order to minimize the potential of tissue damage due to confining the power of the incident beam to a smaller area (spot) can also be important. However, even a smaller diameter spot of laser excitation light incident on the tissue spreads to cover a larger area typically ½-1 mm diameter because of elastic scattering turbidity, thus mitigating this consideration. In a preferred embodiment a larger diameter fiber, or a distributed array of smaller fibers can be used. Preferred embodiments balance the fact that low NA fibers typically exhibit an increased spectral background caused by dopants used in the core and cladding of the fiber to reduce the NA, and hence, use a modest core size and NA for the excitation fiber.

For the collection fibers the situation is different. The Raman energy collected is proportional to the square of the NA. Therefore, from a signal-to-background analysis there is an advantage in using high NA collection fibers the size of which is limited by the spectrograph NA. Here, the best choice of fiber NA and fiber diameter is determined by the spectrometer NA, the desired spectral resolution, and considerations of matching optics, as well as the limitation set by filter acceptance angle. In a preferred geometry, one or a few number of delivery fibers are used as the energy of the laser source can be efficiently coupled into the delivery fiber/fibers. However, a greater number of collection fibers is important to increase the area of collection as shown in FIG. 10B. The area for collection is maximized since it is important to optimize collection of Raman light. Taking all these considerations into account, it is best to use as much of the available cross-sectional area of the optical fiber probe for collection fibers, keeping the number and diameter of the delivery fiber(s) to a minimum.

Preferred embodiments include the following trade-offs. For the spectrometer chosen, the desired resolution determines a slit width. Considering the throughput theorem, the requirement on the collection fibers is that the product of fiber NA and diameter equal the product of spectrometer NA and slit width. If it is possible to choose a fiber that satisfies a stronger condition that the fiber diameter equals the slit width and the fiber NA equals the spectrometer NA, the necessity of using matching optics is eliminated and the probe can be directly coupled into the spectrometer. If only the product requirement can be satisfied, matching optics are needed. At the output end, the collection fibers are arranged in a straight line, which is imaged onto the entrance slit by the matching optics. Occasionally spectrometers use curved slits; the output end of the collection fibers can be modified to match any slit shape. An upper limit on the number of collection fibers is that the height of the fiber array image be less than the slit height or CCD chip, whichever is less. However a smaller limitation may be set by the space available in the collection tip.

In a preferred embodiment, the fiber section of the probe includes a single central excitation fiber with an NA of 0.22 and a core diameter of 200 µm. The buffer of the fiber is matched to the diameter of the excitation filter rod, to facilitate proper fiber/filter registration, and has an aluminum jacket to provide optical isolation from the collection fibers. The 200 µm core diameter collection fibers are arranged in two different geometries in two alternate embodiments. The first embodiment consists of two concentric rings of 10 and 17 fibers for the inner and outer ring, respectively. The second embodiment has a single ring of 15 collection fibers. Although the second design has a slightly reduced collection efficiency, it is more flexible and still able to collect a high SNR spectra in short exposure times. The collection fibers all have an NA of 0.26 so that they are f/#-matched to the spectrograph for optimal throughput. The diameter of the probe in a preferred embodiment is less than 2 mm to prevent obstruction of the imaging channel through the speculum of the otoscope.

A preferred embodiment provides flexibility with respect to the particular choice of optics for high-throughput collection so that a variety of optical elements can be used to collect the desired AΩ-product. In a preferred embodiment, a ball lens provides highly efficient collection for front viewing optical fiber probes that closely match calculated collection over a radius of 0.35 mm for blood tissue (0.4 mm for artery tissue) while still collecting over large angles. Collection efficiencies greater than 30% are achieved if a small space is maintained between the sample and lens, greater than 10% when in contact with tissue, the likely and more reproducible in-vivo geometry.

FIG. 10A shows a longitudinal view of the probe tip, while FIG. 10B shows a cross-sectional view at the level of the fiber-filter interface. There is a central excitation fiber with an aluminum jacket for optical isolation to prevent cross-talk with the collection fibers. This fiber is placed in registration with the short-pass excitation rod. The rod is placed inside the long-pass collection filter tube with the two being optically isolated by a metal sleeve. The excitation fiber is then buffered out to ensure proper alignment of the collection fibers, which are registered with the center of the long-pass filter tube. The central excitation fiber has a 200 µm core with a 0.22 NA. The collection fibers are also 200 µm core, but have a 0.27 NA which is closely matched to that of the spectrograph. The filters are secured to the fibers with an index-matching optical cement and the entire fiber bundle/filter module is encased with black Teflon for binding and protection. The probe length is 4 meters.

The filter rod and tube are 1 mm in length ensuring proper spatial placement of the sapphire ball lens. This geometry addresses two considerations. First, at this fiber-lens separation, the excitation light is roughly collimated and not focused to a tight spot on the tissue, thereby reducing the energy density incident upon the sample and preventing possible damage. Second, excellent coupling of the Raman scattered light into the collection fibers is ensured because the ball lens transforms the large angular distribution emerging from the tissue into a well collimated beam that falls within the fiber NA. The ball lens is secured into a crimped stainless steel tube with epoxy, which ensures that no fluid leaks into the tip. The stainless steel tube is then affixed to the fiber-bundle/filter assembly. In order to maximize the ball lens collection efficiency, there are no adherents used on the inner surface.

The total diameter of this probe is under 3 mm. The current size-limiting factor is the diameter of the ball lens, which is 2 mm to accommodate the entire width of the filter tube. This filter size was chosen because this geometry is used to construct Raman probes with two rings of collection fibers (a total of 27 fibers), which more fully utilizes the spectrograph throughput. In practice, a single-ring probe can be used because it provides excellent signal collection and is much more flexible and easier to construct. Recent studies have shown that the probe diameter can be reduced without significantly degrading the collection efficiency. The diameter of the central collection rod was chosen to be 0.55 mm for ease of construction. All components of the probe are constructed of medical grade materials that can withstand standard cold gas ethylene oxide sterilization for surgical procedures.

Figure 10C:
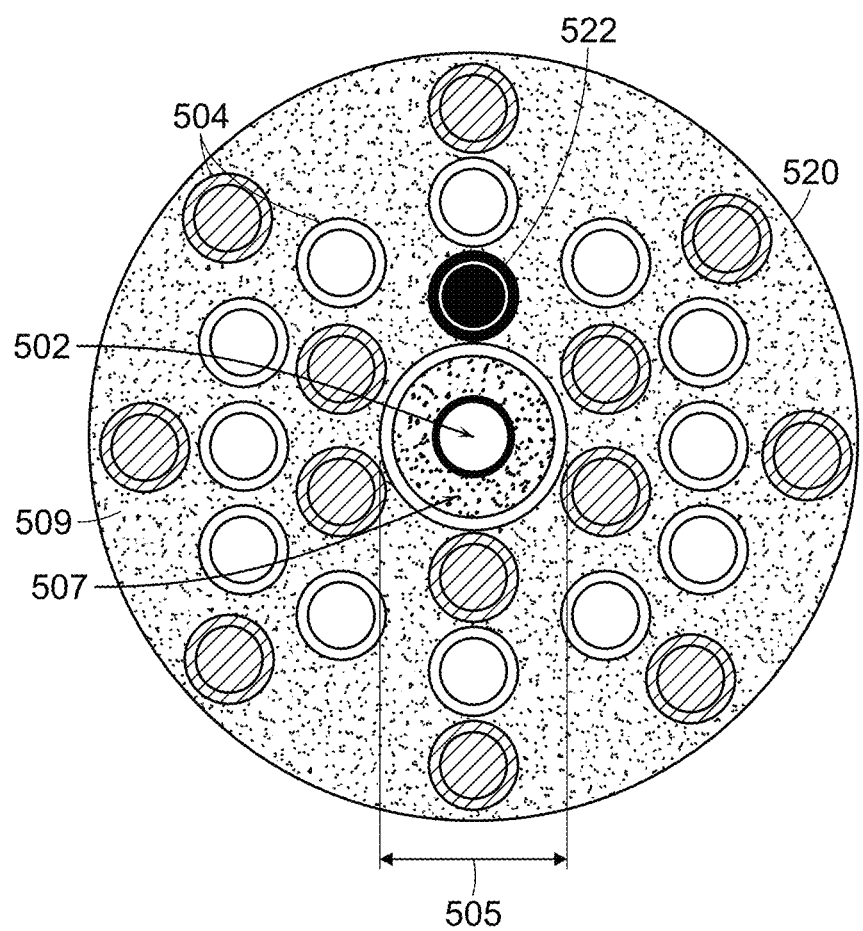
FIG. 10C illustrates an end view of an alternative embodiment of a fiber probe for illumination and collection of light according to the present disclosure.

FIG. 10C shows an end view of a fiber probe 520 according to various embodiments. In some embodiments, a central optical fiber 502 can provide illumination. As shown, some of the collection optical fibers 504, 522 can have different filters or coatings applied at the end to allow different wavelength bands of light to pass through the end of the fiber. The collection optical fibers 504, 522 can be embedded in a first material 509 while the excitation fiber 502 can be embedded in a second material 507. A sleeve 505 can separate the first material 509 and the second material 507. In various embodiments, the first material 509 and the second material 507 can have different reflectivities or indices of refraction.

Figure 11:
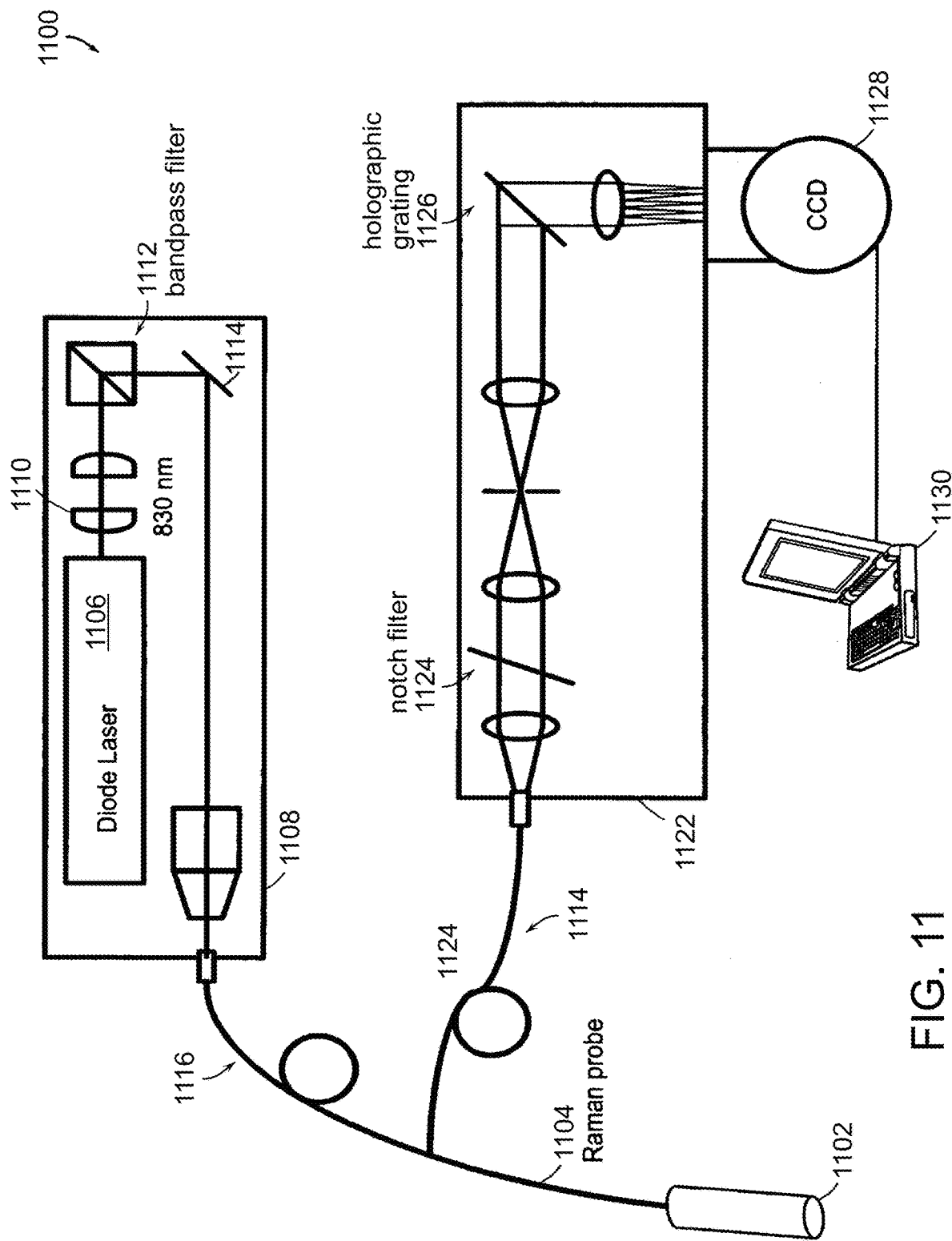
FIG. 11 illustrates a schematic of a system for acquiring Raman spectral data from a patient in accordance with various embodiments of the present disclosure.

FIG. 11 includes a schematic diagram illustrating a system 1100 including a fiber probe 1102 in accordance with preferred embodiments of the invention. A light source system 1108 is coupled to one or more delivery optical fibers 1116 which delivers excitation light through probe 1102 onto a tissue region to be measured. The probe 1102 can be positioned within a speculum as described above with reference to FIGS. 2A, 2B, 9A, and 9B. The light source system 1108 may use a range of illumination sources 1106 depending upon the desired application. Illumination sources 1106 include, but are not limited to, broadband lamps, narrow-line lamps, and a range of laser sources (e.g., gas, solid-state, dye, or diode lasers). In a preferred embodiment, the illumination source 1106 emits at a wavelength longer than 750 nm such as when an argon-pumped Ti:sapphire laser system or a diode laser is used. The diode laser may be an InGaAs laser emitting at 785 nm or 830 nm. Light from the illumination source 1106 can pass through a number of optical elements including lenses 1110, beam-splitters, or mirrors. The light can be filtered by a bandpass filter 1112 and can be coupled into the delivery optical fibers 1116 which are connected to the probe 1102.

The fiber probe 1102 can deliver light to the tissue. Raman-scattered light from the tissue can be collected by one or more collection optical fibers 1114. The collection optical fiber(s) 1114 couple light from the tissue region to a spectral detection system 1122. In the spectral detection system 1122, the light may pass through a notch filter 1124 and can be projected onto an entrance slot of a spectrophotometer. The notch filter can, for example, remove Rayleigh-scattered laser light. Inside the spectrograph, a grating 1126 can disperse light onto a CCD detector 1128. The CCD interface and data storage and processing is provided in a computer 1130 such as a personal computer. Raman signals can be read from the CCD 1128, collected by the computer 1130, and stored on computer readable media for later analysis or used for real time analysis in a clinical setting.

Figure 12:
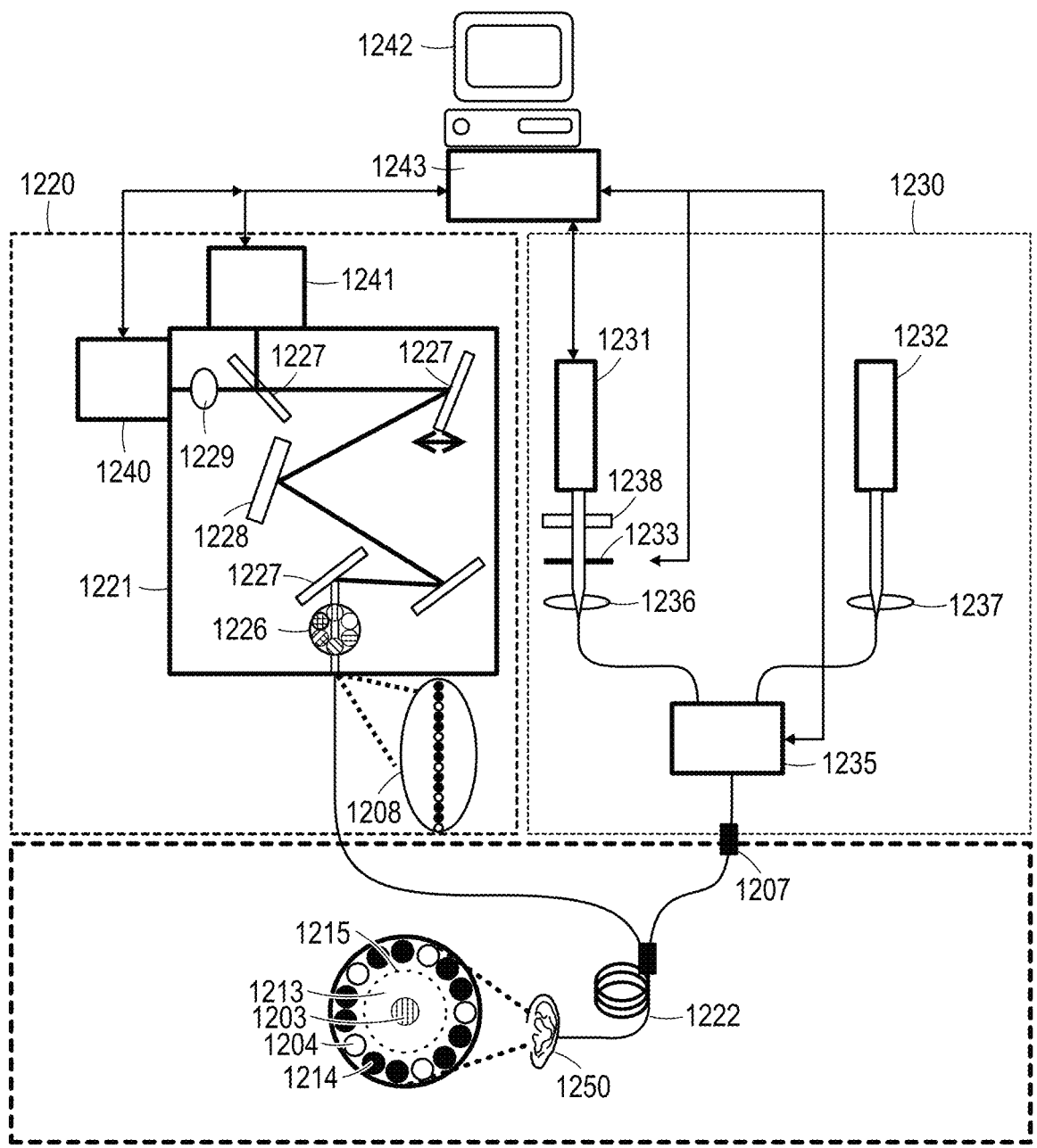
FIG. 12 illustrates a schematic of a system for acquiring Raman and autofluorescence spectral data from a patient in accordance with various embodiments of the present disclosure.

FIG. 12 illustrates a multimodal system including a fiber probe in accordance with various embodiments of the present disclosure. The system can include an excitation portion 1230 and a collection portion 1220. The excitation portion 1230 and collection portion 1220 can provide light to and receive light from the tissue 1250 using a fiber probe 1222. Control of elements of the excitation portion 1230 and the collection portion 1220 can be maintained by a computing device or data processor 1242 through a trigger 1243. In some embodiments, the data processor can be programmed to determine a middle ear disease diagnosis.

The excitation portion 1230 can include one or more illumination sources. In some embodiments, a first illumination source 1231 such as a laser can output light at a specific frequency to stimulate Raman emission in the tissue 1250. In various embodiments, light from the first illumination source can pass through a filter 1238, a shutter 1233, and a focusing lens 1236 that couples the light into an optical fiber that can connect to a fiber switch 1235. The first illumination source 1231 and the shutter 1233 can be controlled by the trigger 1243. A second illumination source 1232 can provide light at a broader frequency to stimulate fluorescence emission in the tissue 1250 or to illuminate the tissue for broadband or white-light imaging. In some embodiments, the second illumination source 1232 can pass through a focusing lens 1237 that couples the light into an optical fiber that can connect to a fiber switch 1235. Although first and second illumination sources are depicted in FIG. 12, some embodiments contemplated herein combine the two separate sources into a single illumination source that can perform all of the duties described herein. The fiber switch 1235 can selectively output light from a chosen illumination source 1231, 1232. Light from the fiber switch 1235 can be coupled from one optical fiber to another using an optional connector 1207 such as an SMA connector. In some embodiments, the optical fiber is continuous from the excitation portion 1230 to the fiber probe 1222.

The collection portion 1220 can include a spectrograph 1221. Light from the tissue 1250 can be collected by the fiber probe 1222 and delivered to the spectrograph 1221 via an array of optical fibers. In some embodiments, the fibers in the array of optical fibers can be arranged in a line to project directly on to the entrance slit 1208 of the spectrograph 1221. Light entering the spectrograph 1221 can pass through a filter wheel 1226. Then, the light can pass through a spectrometer setup including a grating 1228 and several beamshaping or steering elements 1227 including mirrors, lenses, or beamsplitters. The light can be divided into a fluorescence path and a Raman path. The fluorescence path can couple the light directly into a CCD 1243 that is controlled by the trigger 1243. The Raman path can first direct the light through a low-pass filter 1229 before the light is detected at a CCD 1240.

The distal end of the fiber probe 1222 can have various configurations. In an exemplary embodiment, light from the excitation portion 1230 can pass through the excitation fiber 1203 in center portion of the fiber probe 1222. In this embodiment, a ball lens can be used to direct the illumination light at the sample and to collect the light from the sample and focus the collected light into collection fibers.

In an alternative embodiment, the excitation fiber 1203 does not couple directly to an optical element such as a ball lens but instead couples into a ring illuminator 1218. The ring illuminator 1218 can be positioned behind the central flat portion 1213 of a curved window or alternatively through an annular distal lens as described herein. In this embodiment. The window 1213 can have separate flat and annular lens or beam-shaping portions as described in more detail with reference to FIGS. 13B and 13C and can include optical filters. The one or more collection fibers 1204, 1214 can gather the light through the annular lens or beam-shaping portion 1215 of the window and can transmit the light to the collection portion 1220.

In some embodiments, the one or more collection fibers 1204, 1214 can include Raman collection fibers, fluorescence collection fibers, and diffuse reflectance collection fibers. In some embodiments, a filter can be located at a distal end of the each of the collection fibers 1204, 1214. The filters can be different for each of Raman collection, fluorescence collection, and reflectance collection fibers.

Figure 13A:
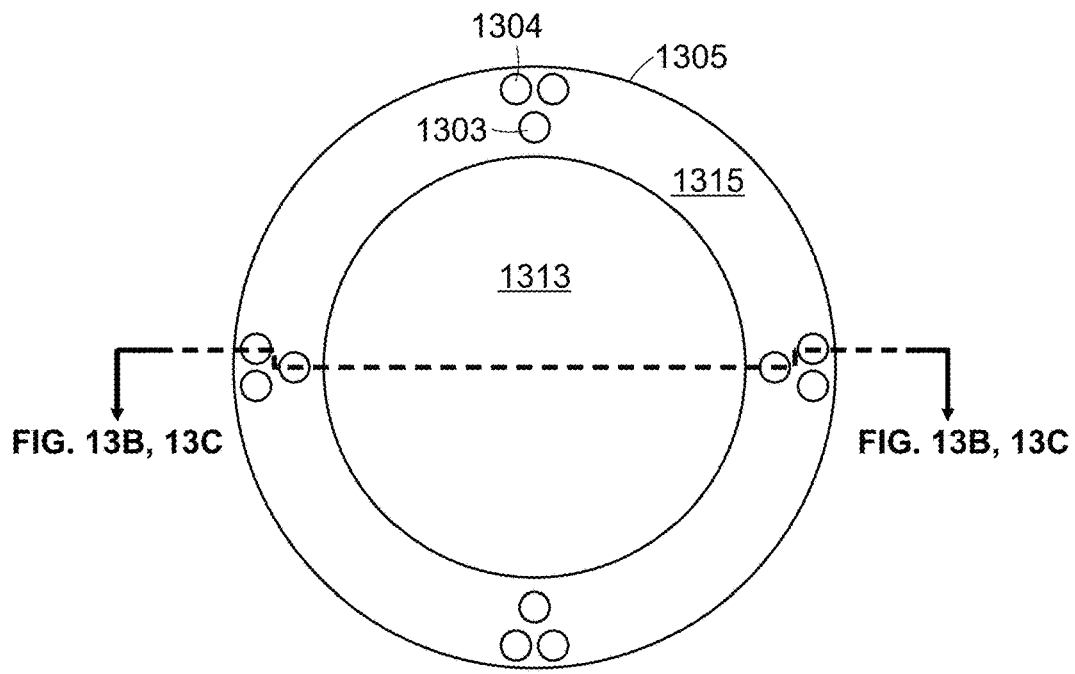
FIGS. 13A-13C illustrate views of a distal end of a speculum having a shaped window in accordance with various embodiments of the present application.

FIG. 13A illustrates an end view of the distal end of a speculum including a shaped window in accordance with various embodiments of the present disclosure. In accordance with various embodiments, light deliver optical fiber(s) 1303 and light collection optical fiber(s) 1304 can be placed side-by-side along a straight line or arc or they can be bunched into concentric rows. In some embodiments, the light delivery optical fiber(s) 1303 can be placed radially inward with respect to the light collection optical fiber(s) 1304. The distal end of the speculum can be sealed using a window 1305.

Figure 13B:
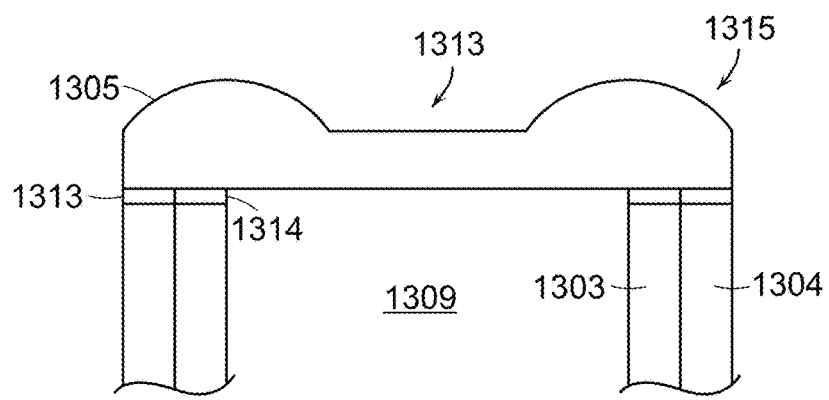

FIG. 13B illustrates a side view of an embodiment of the distal end of the speculum of FIG. 13A in accordance with various embodiments of the present disclosure. The window 1305 can have two sections: a flat section 1313 and a beam-shaping section 1315. The flat section 1313 allows light from the tissue to pass directly through and into the interior 1309 of the speculum where it can be imaged by an otoscope. The beam-shaping section 1315 can be curved to spread light emerging from the illumination optical fiber 1303 or to collect light and direct it towards the collection optical fiber 1304. Although the beam-shaping section 1315 is shown as a single continuous surface, the beam-shaping section 1315 can also comprise individual lenslets or discontinuous structures such as lens sections. In some embodiments, the beam-shaping section 1315 can comprise diffractive structures such as gratings.

Figure 13C:
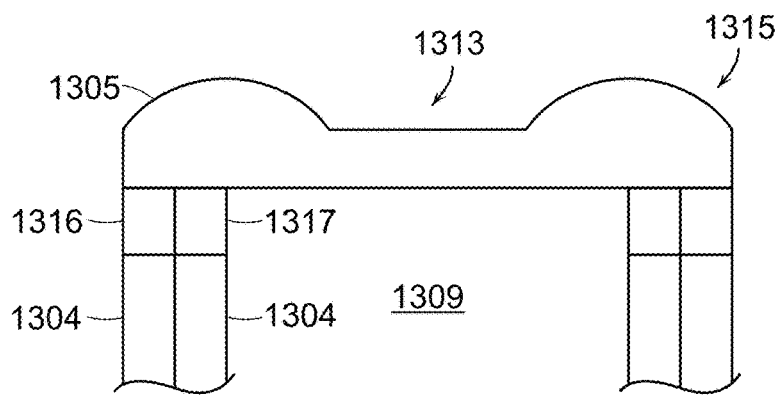

In accordance with various embodiments, the illumination optical fiber(s) 1303 can be coated at the distal end(s) with a first filter material 1313 and the collection optical fiber(s) 1304 can be coated at the distal end(s) with a second filter material 1314 as shown in FIG. 13B. FIG. 13C illustrates a side view of an alternative embodiment that includes a first filter tube 1316 and a second filter tube 1317.

Figure 14B:
FIGS. 14A and 14B illustrate white-light images of middle ear tissue subsequently diagnosed with cholesteatoma and myringosclerosis, respectively.
Figure 14A:
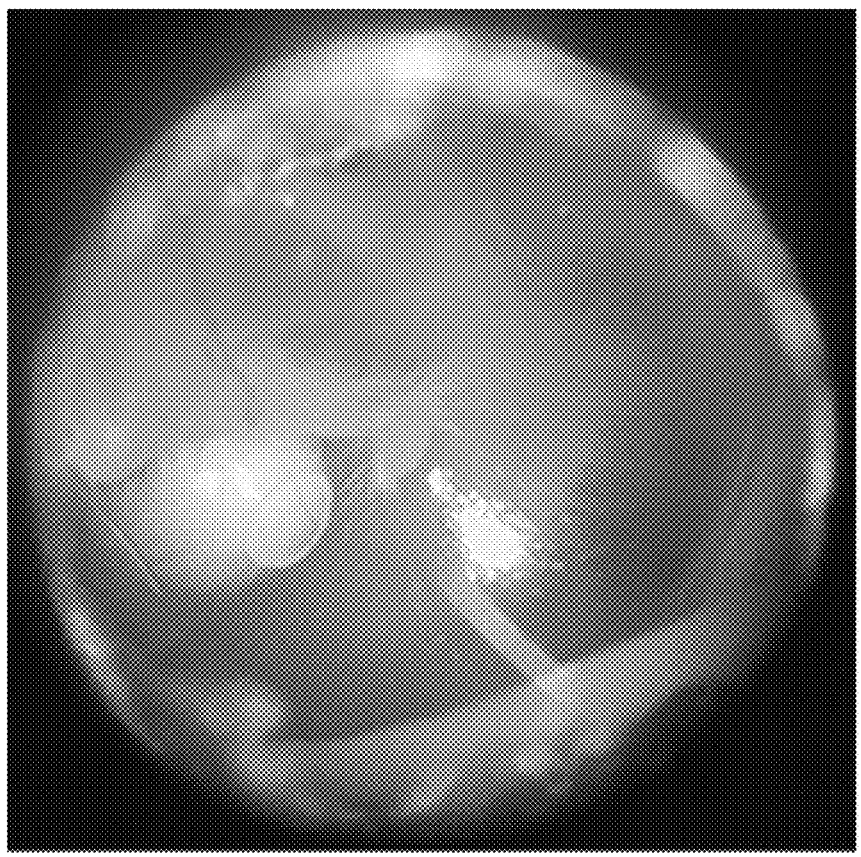

FIGS. 14A and 14B shows representative white light images of a cholesteatoma (A) and a myringosclerosis lesion (B) in situ before surgical excision. In some embodiments, white light images similar to those shown in FIG. 12 can be obtained using the otoscope 100 or endoscope 300 as described previously. In various embodiments, reflected white light from the tympanic membrane can pass through the window 105, 305, other optical or beamshaping elements 327, or the filter wheel 326 before forming an image for a human or machine viewer (e.g., a camera 340).

Figure 15A:
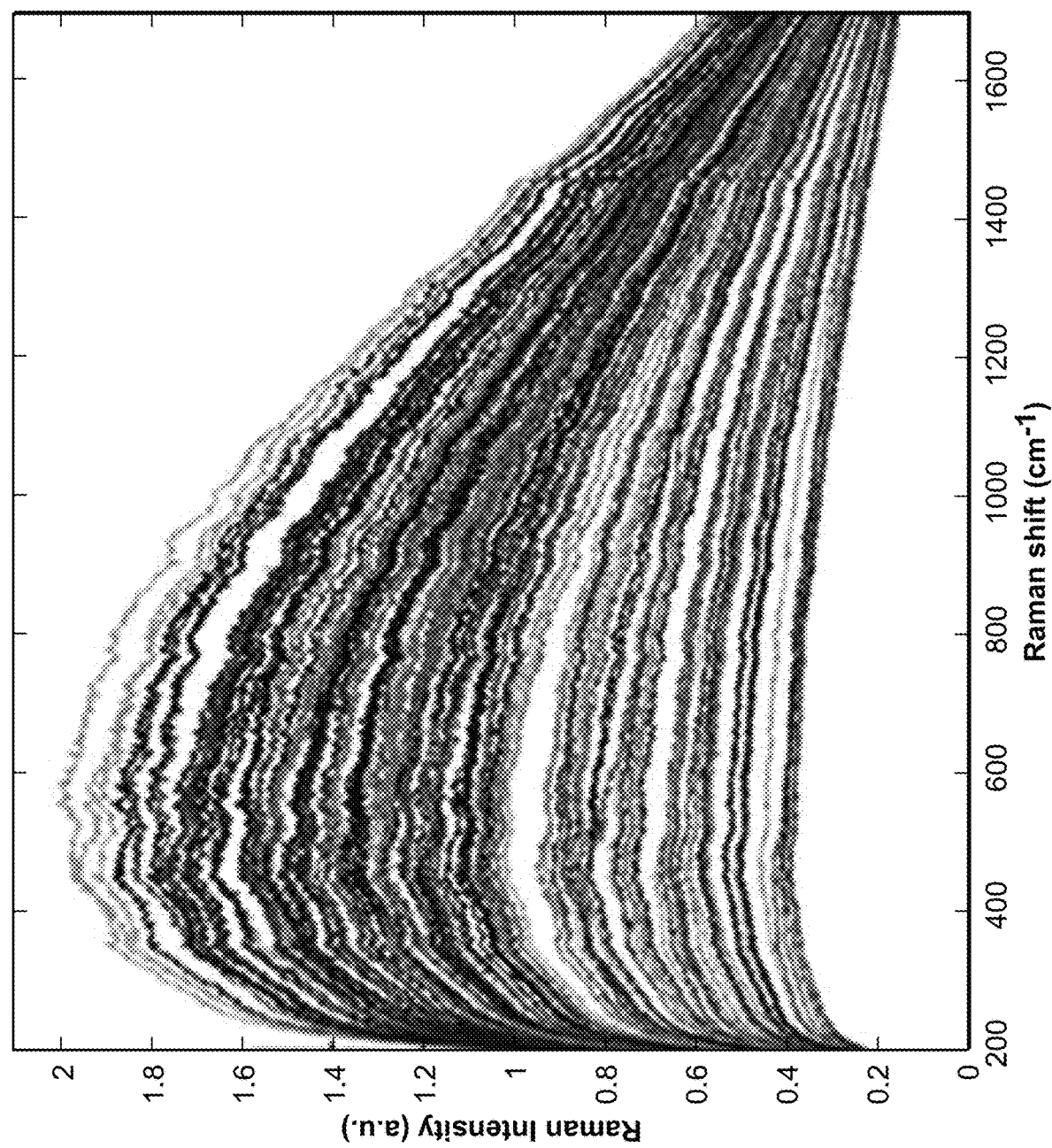
FIGS. 15A-15C illustrate exemplary Raman spectra obtained from tissue associated with cholesteatoma, myringosclerosis with mineralization, and myringoscleroscis without mineralization, respectively.
Figure 15B:
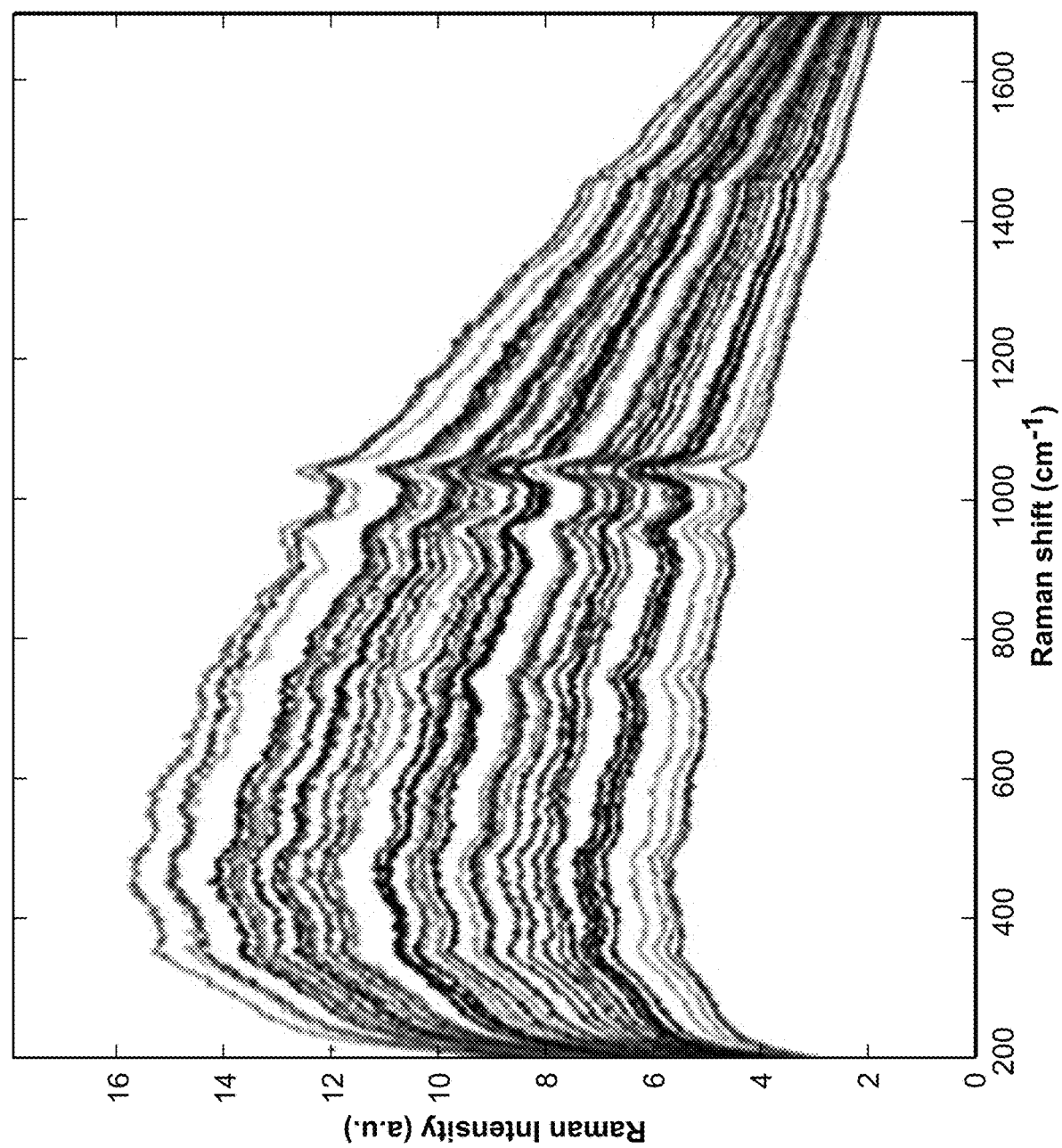
Figure 15C:
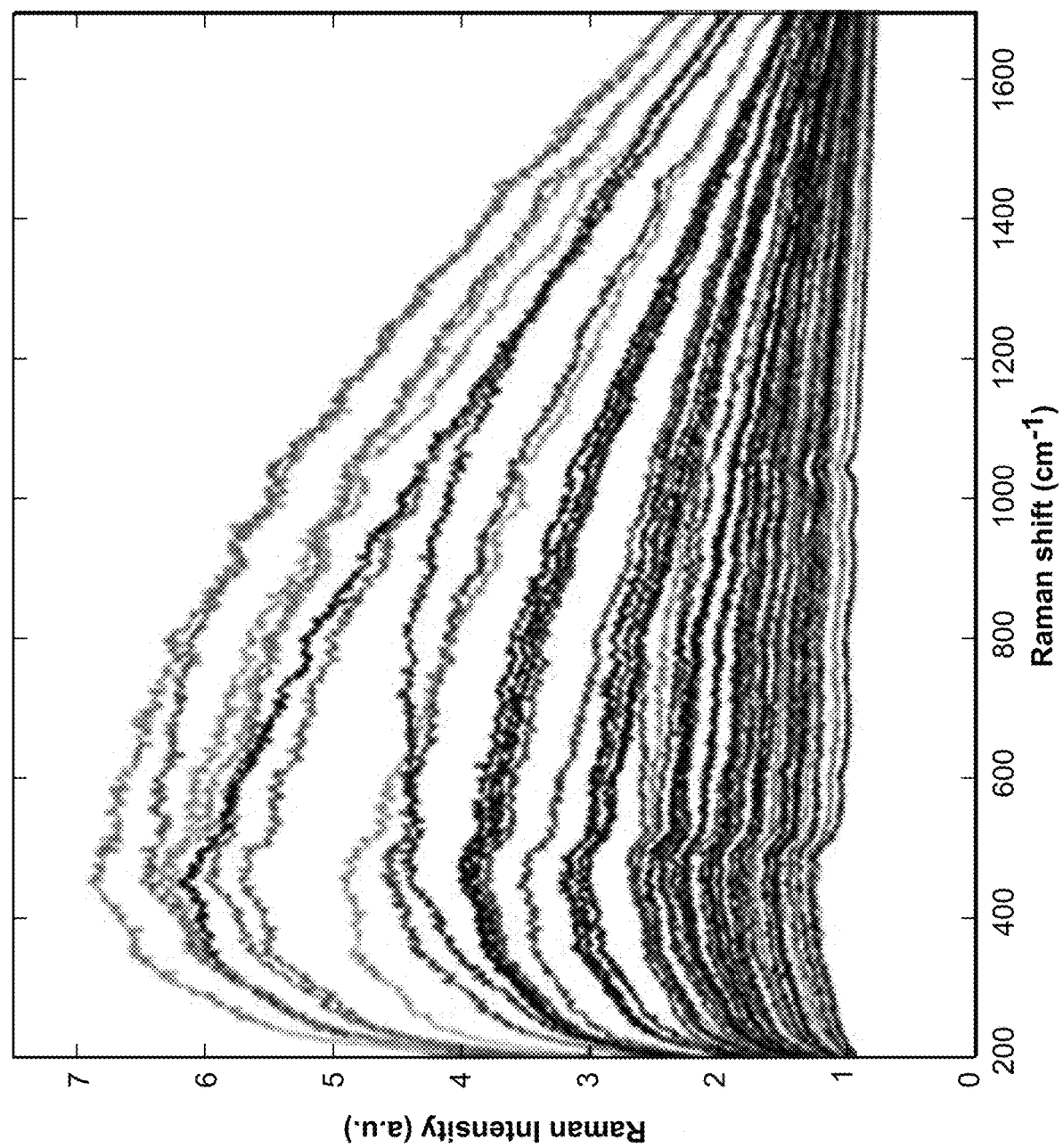

FIG. 15 shows representative Raman spectra acquired from clinical tissue specimens post resection. The specificity of Raman spectroscopy in detecting molecular phenotypes of tissue reveals clear differences in the spectral signatures between the cholesteatoma lesions (FIG. 15A) and some of the myringosclerosis sites (FIGS. 15B and 15C). This is consistent with the medical consensus on these two pathological conditions, where the former is characterized by intrusions of keratinizing stratified squamous epithelium supported underneath by loose connective tissue (constituted largely by collagen and elastin) while the latter is comprised of calcified plaques amidst collagen deposits. Since the myringosclerosis lesions display significant heterogeneity in the spatial distribution of the calcified structures, treating the acquired spectral set from such tissue specimen as a homogeneous bucket would provide an inaccurate representation. Thus, based on the differences within the myringosclerosis set (particularly in the well-characterized Raman feature at 960 cm$^{-1}$), we separated the mineralized sites (FIG. 15B) from the grossly uninvolved tissue (FIG. 15C) using peak identification code over a 20 cm$^{-1}$ band centered at this feature. It is worth noting that the datasets show a measure of overlap that can be attributed to a continuous pathology model from uninvolved tissue to a site with high concentration of calcified structures. The differences, if any, between the cholesteatoma samples and the non-mineralized myringosclerosis set are more subtle and within-class variations in the spectral dataset impede the possibility of elucidating such differences by single-feature analysis alone.

Figure 16A:
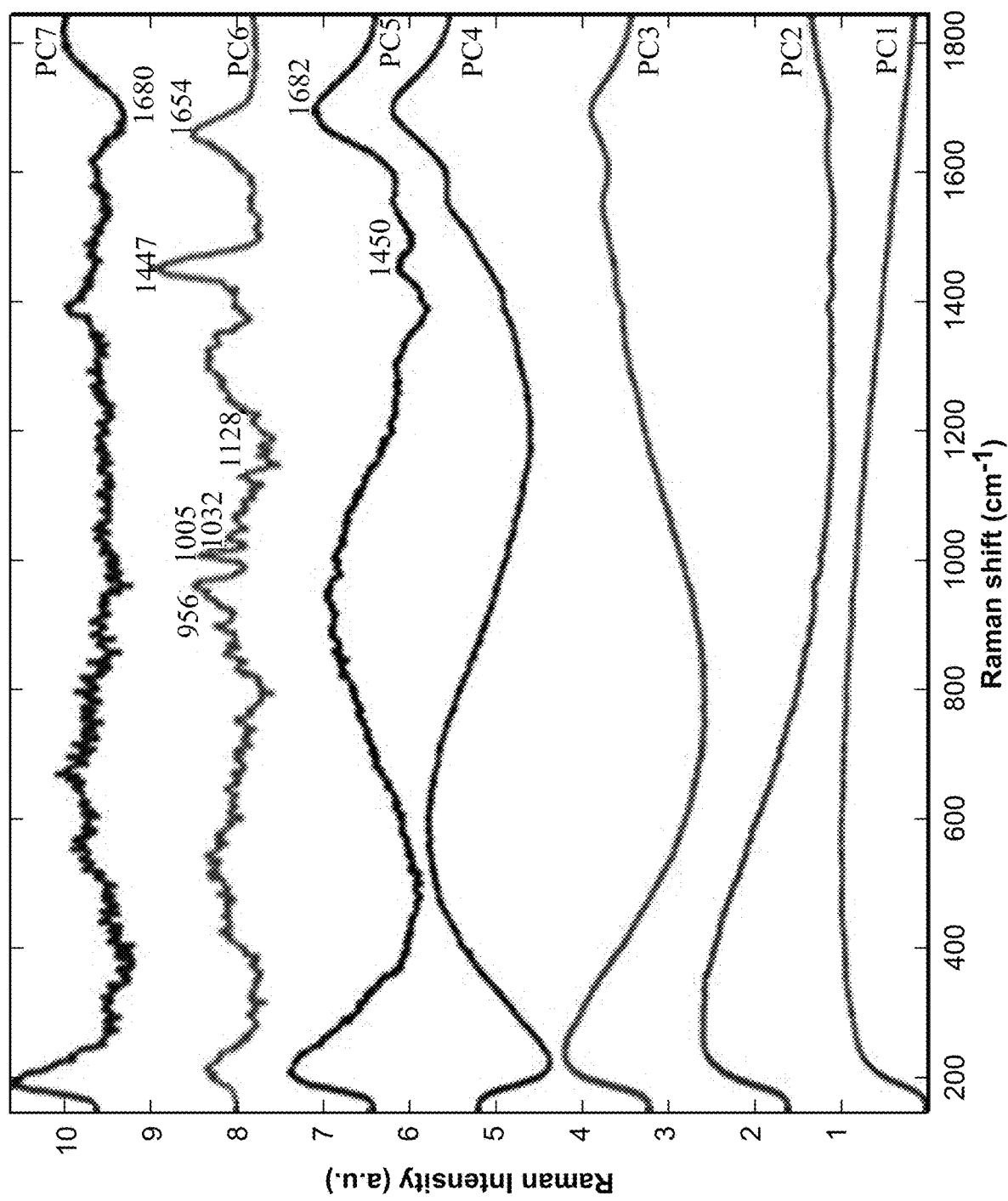
FIGS. 16A-16C illustrate principal components of Raman spectra obtained from tissue associated with cholesteatoma, myringosclerosis with mineralization, and myringoscleroscis without mineralization, respectively.
Figure 16B:
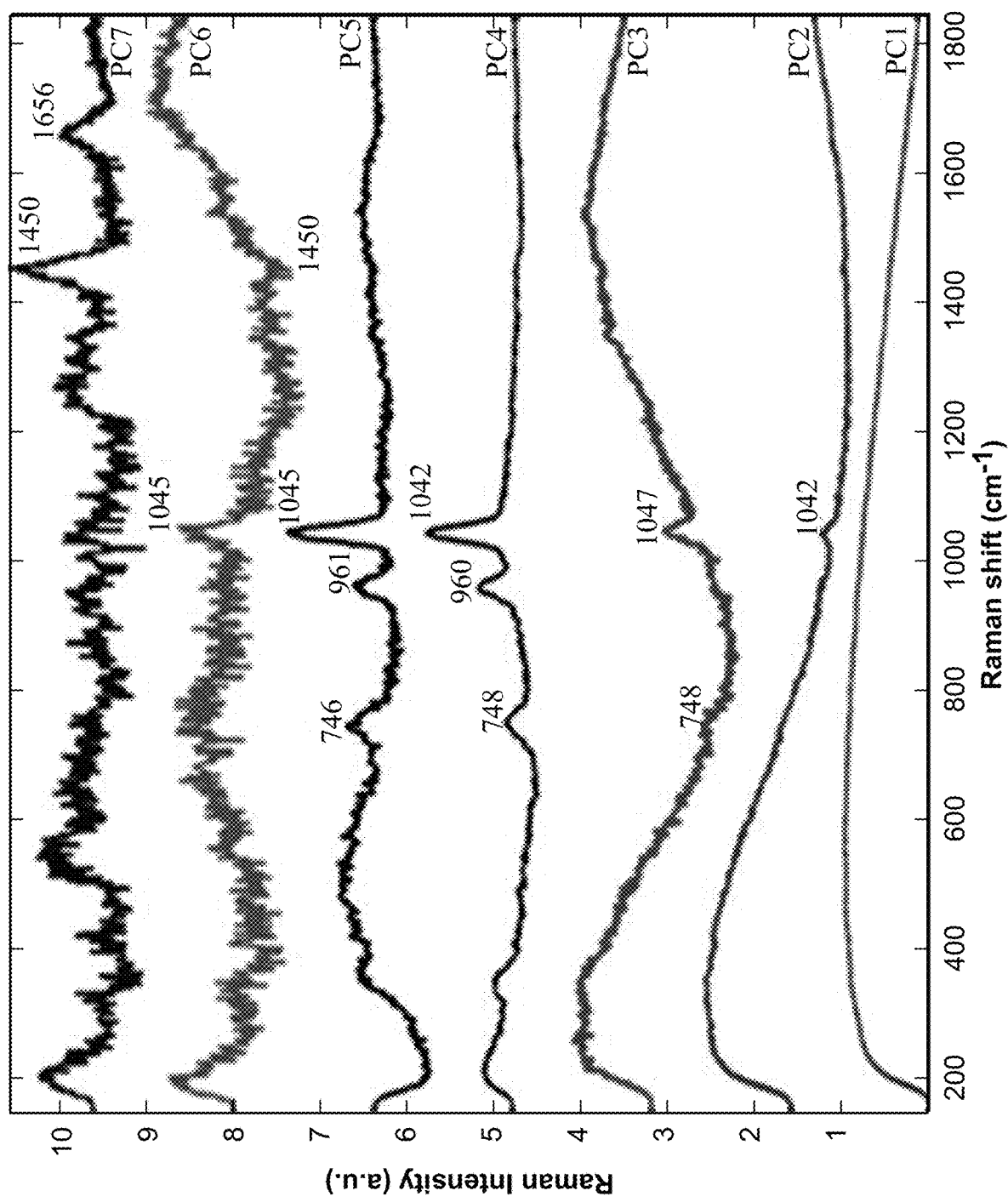
Figure 16C:
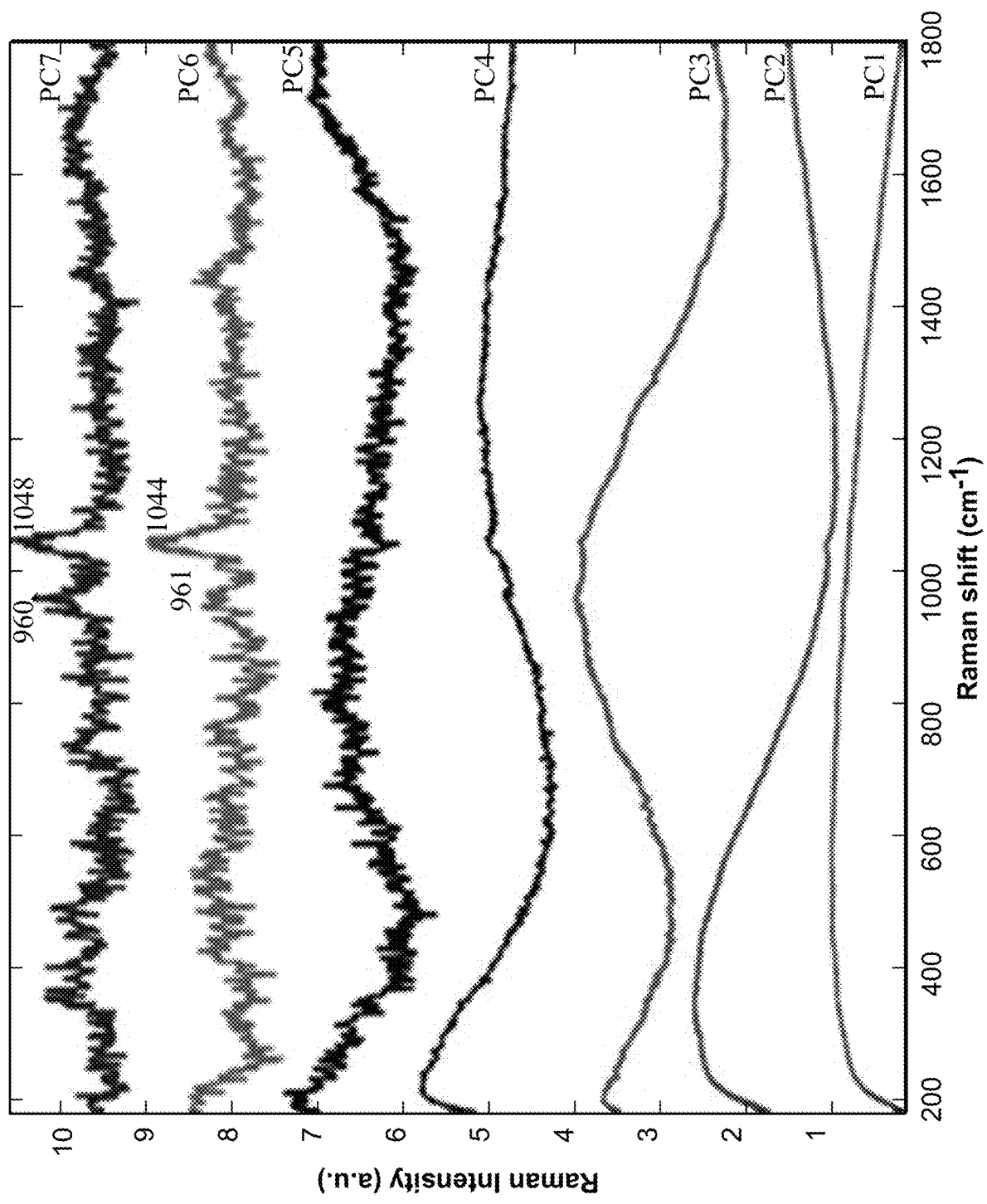
Figure 16D:
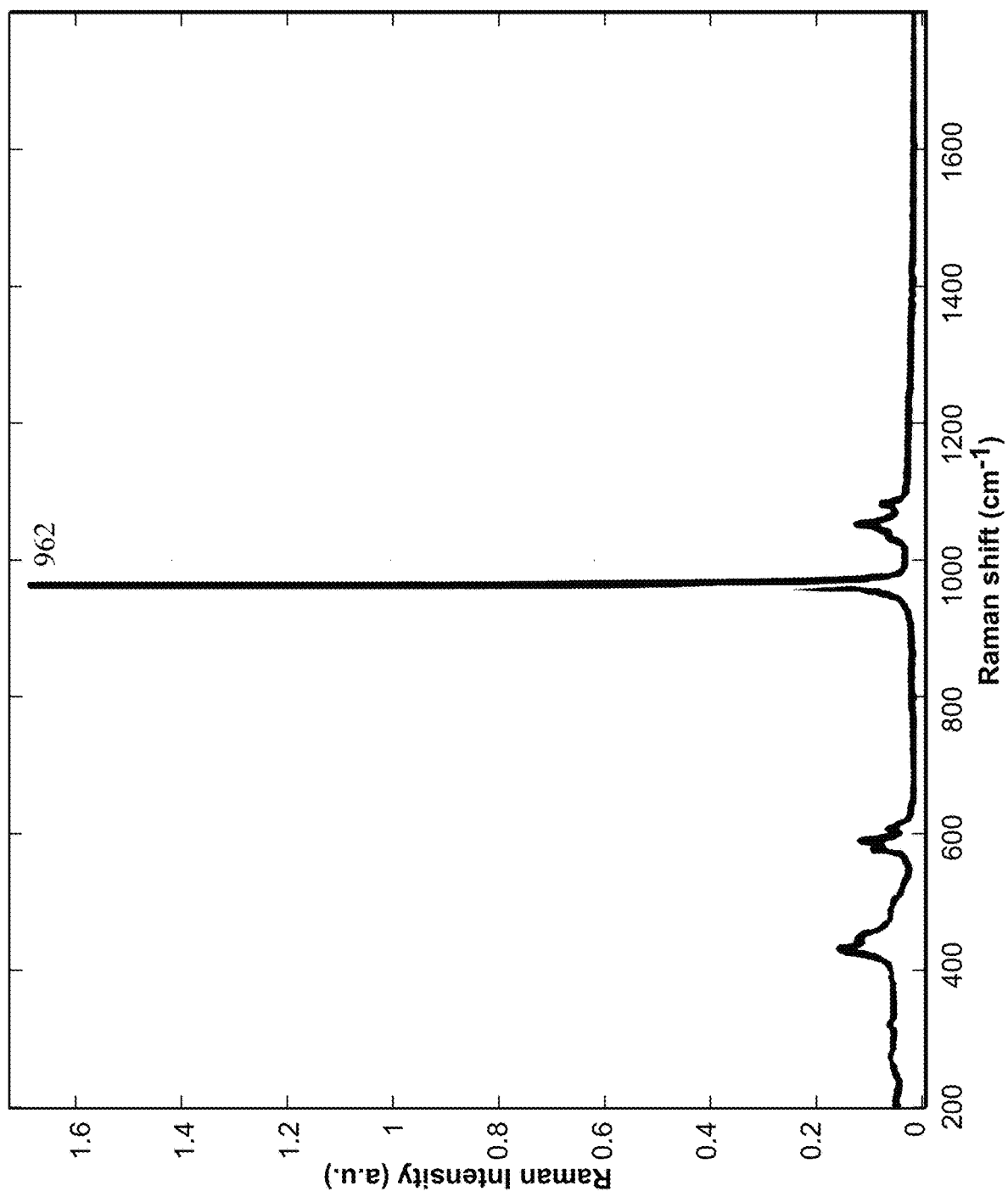
FIG. 16D illustrates an exemplary Raman spectrum of pure stoichiometric calcium hydroxyapatite.

In some embodiments, principal components analysis (PCA) can be employed to reduce the dimensionality of the spectral data into a few critical components that explain most of the data variance and to help identify "spectral markers" that can reliably discern the tissue pathology. FIGS. 16A-16C show the first 7 principal components (PCs) for each of the three tissue types (cholesteatoma in FIG. 16A, biomineralized sites of myringosclerosis in FIG. 16B, and uninvolved sites of myringosclerosis lesions in FIG. 16C) with the labels highlighting the Raman scattering features in the pertinent PC loadings. FIG. 16D illustrates a Raman spectrum acquired from pure stoichiometric calcium hydroxyapatite for comparison. The broad autofluorescence background provides a significant contribution to the first few PCs for each tissue type despite the use of the NIR excitation source. Shot noise associated with the autofluorescence background in the visible region can significantly impede the classification accuracy thereby highlighting the importance of working in the "tissue-transparent" IR window.

The PC loadings for the cholesteatoma sites (FIG. 16A) exhibit Raman features of keratin and collagen as the main structural components of such lesions including 1005 cm$^{-1}$ (C—C stretching vibration of the aromatic ring in the phenylalanine side chain), 1447 cm$^{-1}$ (methylene, CH$_2$, deformation band (scissoring)) and 1654 cm$^{-1}$ (v(C=O) stretching amide-I band). Weaker features at 956 cm$^{-1}$ (CH$_2$ rock), 1032 cm$^{-1}$ (C—H in-plane bending mode of phenylalanine) and 1128 cm$^{-1}$ (skeletal C—C mode, trans conformation) are also visible. These observed features are in agreement with those reported in the literature. It is worth noting that some of these features can also be indicative of the presence of lipids (e.g. cholesterol and cholesterol ester). Additionally, in relation to the amide-I vibration, we interestingly observe two potential features, one at 1654 cm$^{-1}$ (α-helix) as previously noted and another at ca. 1680 cm$^{-1}$, which suggests the existence of alternate conformations of the structural proteins in the lesion. This is not surprising given the continuous collagen degradation and bone resorption processes during the progression of this proliferative lesion.

While gross inspection of the myringosclerosis lesions revealed some differences from cholesteatoma cases, PCA of the myringosclerosis sites with and without mineralization reveals dramatic differences in the underlying biochemistry. Outside of the broad autofluorescence background, the myringosclerosis sites consisting of mineralized clusters displays little in common with the aforementioned cholesteatoma features—even though both look nearly identical under white light otoscopic examination (FIGS. 14A and 14B above). In particular, PCs as shown in FIG. 16B highlight an intense peak at ca. 1044 cm$^{-1}$ with another strong peak at 960 cm$^{-1}$ and a less intense feature at 748 cm$^{-1}$. Since the formation of calcium phosphate plaques in the lamina propria of the tympanic membrane is well-known in myringosclerosis, the presence of the 960 cm$^{-1}$ peak, the $v_1(PO_4)$ totally symmetric stretching mode of the "free" tetrahedral phosphate ion, is expected. Finally, PC loadings 6 and 7 also exhibit Raman features at 1447 and 1654 cm$^{-1}$, albeit at much smaller intensities than for the aforementioned peaks observed in PCs 3-5, indicating the presence of loose connective tissue. On the other hand, FIG. 16C shows that the PC loadings corresponding to sites with little or no mineral components (as verified on histological examination) display noisier profiles. Nevertheless, the presence of the weak features at 960 and 1048 cm$^{-1}$ in PC7 indicates that morphologically uninvolved tissue, particularly at lesion margins, may be biochemically distinct from normal tissue, i.e., molecular modifications in the margins could be the precursors of lesion development.

Of considerable interest is the presence of the 1044 cm$^{-1}$ that has, thus far, not been identified in the literature in the context of middle ear pathogenesis. Given the intensity of these peaks, especially the 1044 cm$^{-1}$ feature, one can reasonably infer that it emanates from a Raman-active mineralized constituent as opposed to the surrounding protein matrix. In fact, biological apatite is a poorly crystalline, non-stoichiometric material (Ca:P molar ratio <1.67) that may contain additional ions in the structure such as Na$^+$, SiO$_4^{4-}$, CO$_3^{2-}$, Zn$^{2+}$ and Mg$^{2+}$. By examination of the acquired spectra and its comparison with that of pure stoichiometric calcium hydroxyapatite (FIG. 16D), it is evident that the structures in these lesions are not composed solely of apatite. For example, there is considerable broadening of the 960 cm$^{-1}$ band in the acquired spectra in relation to the sharp feature obtained from pure apatite to the extent that another phosphate $v_1$ mode that occurs at 948 cm$^{-1}$ is obscured by the broad phosphate stretching mode at 960 cm$^{-1}$. An analogous finding of phosphate peak broadening has been reported in type II microcalcifications in breast tissue, where the introduction of carbonate ions into the apatite structures has been correlated with increasing malignancy of the lesion.

We hypothesize that similar anionic substitutions are prevalent in the calcium phosphate plaques in myringosclerosis. The 1044 cm$^{-1}$ peak can then be attributed to the presence of asymmetric stretching ($v_3$) of the P—O bond observed in carbonate-and silicate-substituted phosphate with the relative strength of this peak in relation to 960 cm$^{-1}$ depending on degree of substitution. Furthermore, based on the absence of strong carbonate peaks at 912 and 1477 cm$^{-1}$, we are of the view that the silicate-substitutions dominate the biomineralized constituents in these lesions. At this point, it is important to consider the possible origin(s) of such apatite structures and, critically, the presence of silicate-substitutions from a pathophysiological perspective. The most imperative condition for apatite formation is an exceedance of the critical supersaturation level by the component ions in the microscale milieu Here, the critical supersaturation signifies a value close to the solubility product beyond which the component ions of the crystal do not remain in solution but precipitate and form aggregates. Cartilage fluids are marginally supersaturated with CaPO$_4$, the principal component ion of biological apatite, but do not crystallize in physiological conditions due to the presence of various chelators and crystallization inhibitors. However, a pathological condition such as chronic otitis media or the sudden insertion of a tympanostomy tube (grommet) could shift the supersaturation level towards a higher ionic disequilibrium, producing an environment that favors apatite formation. Additionally, emerging data from in vitro model studies of mammary cell mineralization suggest that the presence of hydroxyapatite crystals in the extracellular matrix could, in turn, enhance the proliferation of the lesion.

Contrary to apatite, the biochemical origin and clinical relevance of silicate substitutions in the middle ear are elusive. We hypothesize that the formation of such structures is an end result of severely disrupted cellular homeostasis, a major determinant of which is the presence of silicone tympanostomy tubes. In terms of the impact, soluble silicate ions have been found to stimulate the expression of type-I collagen in osteoblast-like cell cultures. Furthermore, in vivo assessments have demonstrated enhanced bioactivity of silicon-substituted hydroxyapatite over pure hydroxyapatite indicating that growth of such lesions could be faster than those in the presence of purely stoichiometric apatite.

Figure 17A:
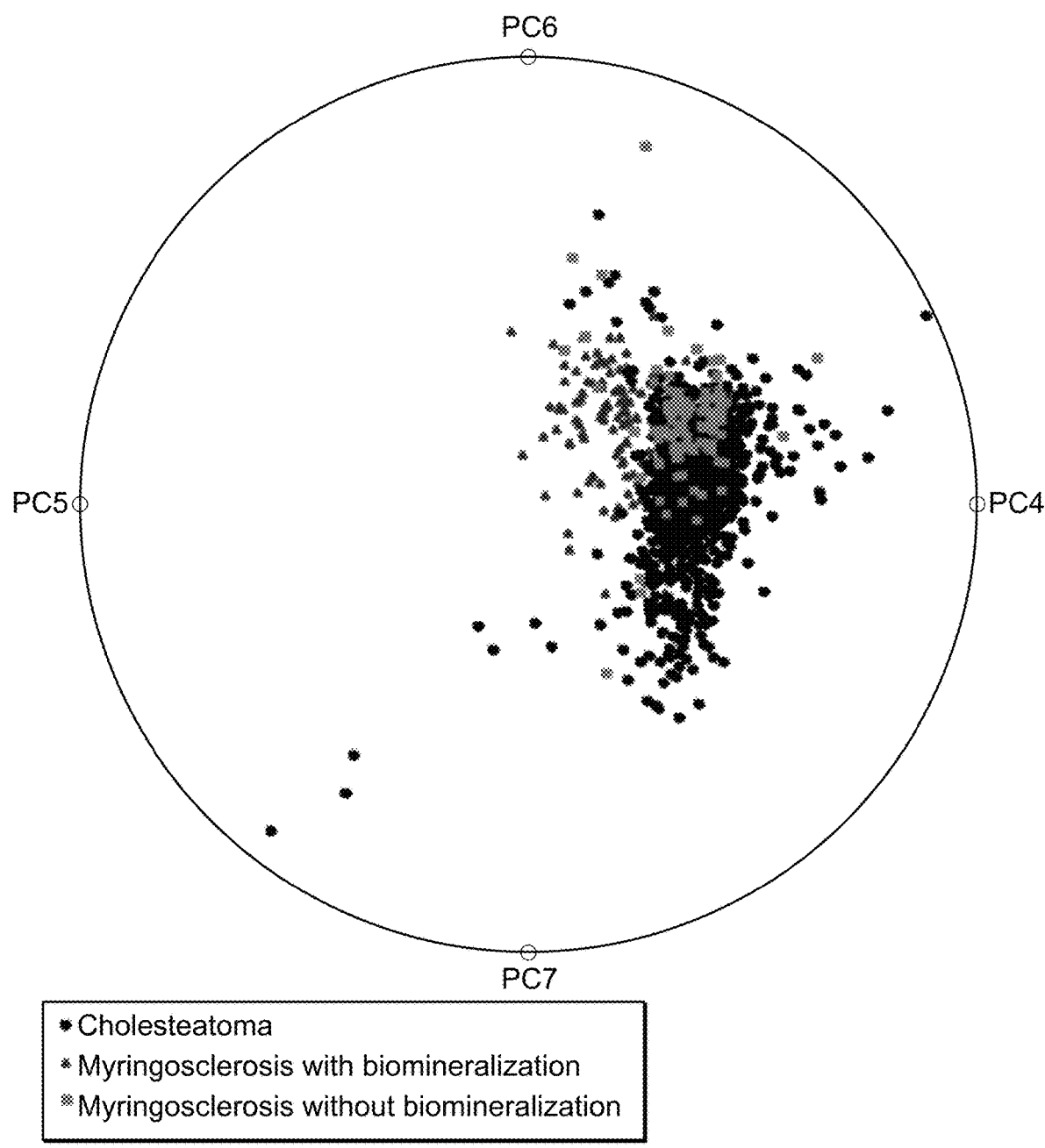
FIG. 17A illustrates a multi-dimensional radial visualization plot of selected principal component scores obtained from a Raman spectral dataset in accordance with certain embodiments of the present application.
Figure 17:
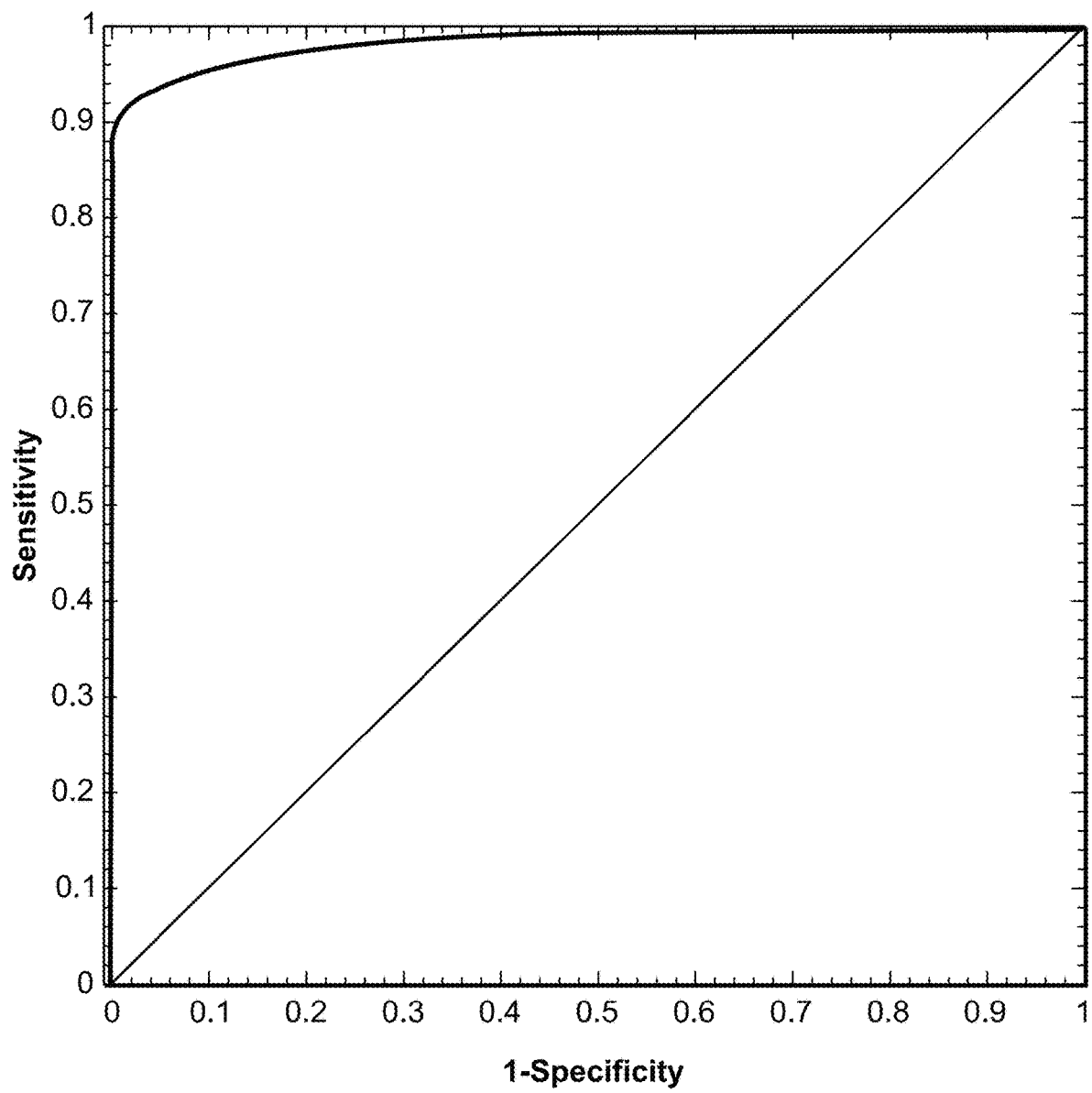
FIG. 17B illustrates an exemplary receiver operator characteristic (ROC) curve for systems and methods described herein.

In addition to identifying a robust set of biologically relevant spectral markers, devices, methods, and systems of the present disclosure can use a decision algorithm that rapidly delineates the pathology of the tissue in a label-free, real-time manner First, a nonlinear radial visualization map can be constructed to plot the PC data dimensions onto a two dimensional space for the purpose of clustering (FIG. 17A). These PC scores were extracted from the entire spectral dataset—and not from separate loadings as identified in FIG. 14. The PCs describing tissue site biochemical characteristics are equally spaced around the perimeter of a circle and provide dimension anchors, where the values of each dimension (PC score) are standardized between 0 and 1. Each tissue site is shown as a point inside the unit circle with its location governed by its dimension anchors. The radial visualization plot reveals an almost clearly separable cluster for the biomineralized myringosclerosis sites with substantial overlap between the cholesteatoma sites and the other myringosclerosis sites, stemming from the lack of distinctive spectral markers that separates the latter two. The few incorrectly segregated myringosclerosis sites can be attributed to the spectroscopy-histopathology registration error. It is worth noting that a high degree of reproducibility when replicate measurements were performed on the same sites in each tissue specimen. Expectedly, the inter-sample variations were larger than the intra-sample changes—which can be attributed to the intrinsic heterogeneity of tissue specimen acquired from different individuals.

To quantify the discrimination ability, PLS-DA decision algorithms were developed and tested in a leave-n-site-out cross-validation routine. First, a subset of cholesteatoma spectra were randomly chosen in order to constrain the number of data points for each class to be comparable. This was undertaken to prevent overtraining that would otherwise skew the prediction results. Second, 60% of the observations from each class were used for PLS-DA model training and the rest were used to constitute an independent test set. These two steps were iterated 100 times each to get a robust estimate of the prediction capability. We computed the average correct classification rates to be ca. 73%, 95% and 76% for cholesteatoma, biomineralized myringosclerosis sites and other myringosclerosis sites without apatite content, respectively. As expected, the myringosclerosis sites showing biomineralization are classified with high accuracy owing to the presence of reliable spectral markers. The robustness of the PLS-DA derived decision algorithm was tested using a negative control study where arbitrary labels were assigned to the spectral data regardless of their true origins. In this case, the average correct rate of classification was found to be ca. 33%, which can be attributed to random chance in picking one correct class out of three. The low value of classification accuracy in the control study confirms the robustness of the algorithm to spurious and chance correlations.

Finally, binary classification models were implemented using only the mineralized myringosclerosis and cholesteatoma data. This yielded positive predictive value (PPV) of 99.02%, negative predictive value (NPV) of 95.63%, sensitivity (SE) of 95.48%, specificity (SP) of 99.06%, and overall accuracy (OA) of 97.27%. When the same algorithm was applied to the mineralized myringosclerosis dataset against spectra from cholesteatoma and other myringosclerosis sites combined, the values of PPV, NPV, SE, SP and OA obtained were observed to be 90.32%, 95.81%, 92.29%, 94.68% and 93.85%, respectively. FIG. 17B shows the corresponding receiver operating characteristic (ROC) curve (plot of sensitivity versus (1-specificity)), where area under the curve is computed to be 0.98 (for comparison, the AUC of a perfect algorithm is 1.00). The slight degradation of the performance due to merging the cholesteatoma sites with the non-mineralized myringosclerosis sites support our hypothesis of possible biochemical changes in the non-mineralized sites in the myringosclerosis tissue prior to their morphologic manifestations.

In the study described above, samples were surgically removed from six patients after white light otoscopic examination by an experienced otolaryngologist. The set of unfixed, de-identified tissue specimens—grossly indicative of cholesteatoma or myringosclerosis lesions respectively—were shipped frozen on dry ice and thawed at room temperature before scanning. To prevent dehydration, the tissues were moistened with a small amount of normal saline. The tissues were placed side-by-side on the scanning platform for Raman spectral acquisition as detailed below. After spectral collection, the samples were fixed in 10% neutral buffered formalin and were paraffin-embedded, sectioned and stained for histopathological analysis. All experiments were performed in accordance with the approved guidelines and regulations.

The samples were placed on quartz cover slips to enable scanning measurements in an inverted geometry and to reduce substrate interference. In order to assess the feasibility of high-throughput measurements, we performed the experiments on a home-built a fiber probe-based flatbed scanner at the MIT Laser Biomedical Research Center. Wide area spectroscopic imaging was achieved by mechanically scanning the beam. Here, a 785 nm compact solid-state laser is used as excitation source and the collected light is recorded on a spectrograph (Holospec f/1.8i, Kaiser Optical Systems) and a thermoelectric-cooled, back-illuminated, and deep depleted CCD (PIXIS: 100BR_eXcelon, Princeton Instruments). The power at the sample was held constant at 70 mW and the spectral recording time was 100 msec/pixel. The recorded spectra were corrected for the presence of cosmic rays before further data analysis and interpretation.

The Raman system was wavenumber calibrated and corrected for the system wavelength response and fiber probe background. The spectral dataset obtained using the scanning platform contained the spectra from tissue and substrate (where tissue was absent) in the area scanned. Due to the possibility of introducing spectral artifacts, no further processing (e.g., removal of the autofluorescence background/baseline correction) was undertaken. To visualize the ability of Raman spectroscopic measurements to differentiate between the pathophysiological sites, principal component analysis (PCA) was employed on the entire tissue spectral dataset. PCA is a widely used data exploration technique and is extensively employed to understand the clustering (or the lack thereof) of high-dimensional spectroscopic data. Radviz, a component of Orange data mining software37, was subsequently used to plot the scores against a set of selectively chosen principal components (PCs) for optimal visualization of the class separation. Finally, partial least squares-discriminant analysis (PLS-DA) was employed to build decision algorithms to quantify the segmentation capability.

While the present invention has been described herein in conjunction with preferred embodiments, a person of ordinary skill in the art can effect changes, substitutions or equivalents to the systems and methods described herein, which are intended to fall within the appended claims and any equivalents thereof.

What is claimed is:

1. A device to detect biological material in an ear of a subject comprising:
    a probe for insertion into an ear canal;
    a first light source to illuminate the biological material at a site within the ear canal for visual examination of a region of interest;
    a spectral excitation light source;
    one or more light delivery optical fibers, the one or more light delivery optical fibers located within the probe and optically coupled to the spectral excitation light source to deliver a Raman excitation light to the biological material;
    one or more light collection optical fibers, the one or more light collection optical fibers located within the probe;
    an imaging detector to detect an image of tissue within the ear canal;
    a spectrometer coupled to the one or more collection optical fibers that receives Raman light scattered from the biological material in the ear canal;
    a spectral detector optically coupled to the spectrometer to detect the received Raman light; and
    a data processor configured to execute instructions to analyze principal components of the detected Raman light to determine a spectral contribution of a plurality of endogenous molecular components within the biological material including at least one molecular component selected from the group of mucin, keratin, apatite, and collagen in the detected Raman light, wherein the data processor generates spectral data corresponding to at least a first principal component and a second principal component that are scored to record a biochemical characteristic of the biological material at the site within the ear canal and thereby generates diagnostic data regarding a pathological condition of the ear based on stored spectral markers corresponding to a plurality of different pathological conditions of endogenous tissue, wherein the spectral markers comprise a cluster map of principle component data; and
    a display connected to the data processor that displays the image of the tissue within the ear canal and the diagnostic data to indicate at least one of the pathological conditions based on the generated spectral data and the stored spectral markers.

2. The device of claim 1 further comprising a sapphire window at a distal end of the probe.

3. The device of claim 1 further comprising one or more optical filters including a filter located at a distal end of the one or more light delivery optical fibers or the one or more light collection optical fibers.

4. The device of claim 3 wherein the one or more optical filters includes a long-pass filter.

5. The device of claim 1 wherein the spectral data includes at least one of fluorescence spectra and Raman spectra.

6. The device of claim 1 wherein the device comprises an otoscope or otoendoscope.

7. The device of claim 6 wherein the otoscope comprises a housing with the imaging detector that generates video images for visual assessments of the middle ear.

8. The device of claim 1 wherein the biological material is a cholesteatoma or otitis media.

9. The device of claim 1 wherein the biological material comprises one or more of keratin, collagen, nicotinamide adenine dinucleotide (NADH), elastin, tryptophan, flavin adenine dinucleotide (FAD), mucin, or porphyrins.

10. The device of claim 1 wherein the biological material is one or more blood analytes.

11. The device of claim 10 wherein the blood analyte is glucose.

12. The device of claim 1 wherein the imaging detector is configured to acquire white-light images of the region of interest.

13. The device of claim 1 wherein the probe is a speculum, the speculum including the one or more light delivery optical fibers and the one or more light collection optical fibers.

14. The device of claim 1 further comprising one or more optical filters that are mounted on a filter wheel disposed within the device.

15. The device of claim 1 wherein the spectral excitation light source includes at least one of a laser or a light emitting diode (LED).

16. The device of claim 1 wherein the data processor is programmed to determine a disease diagnosis of a fluid component of tissue within the middle ear.

17. The device of claim 13 wherein a distal end of the speculum has a diameter in a range of 4 mm-10 mm.

18. The device of claim 1 wherein the spectral excitation light source comprises a Raman excitation light source having a wavelength of at least 700 nm.

19. The device of claim 1 further comprising a lens coupled to distal ends of the one or more light delivery optical fibers, the light delivery optical fibers forming a first concentric ring around a distal window and the one or more light collection optical fibers forming a second concentric ring around the distal window.

20. The device of claim 19 wherein the lens comprises an annular lens that is concentric around the distal window, the annular lens coupled to the light delivery optical fibers and the light collection optical fibers.

21. The device of claim 1 further comprising a fluorescence excitation light source.

22. The device of claim 1 wherein the probe has a reduced diameter at a curved distal end configured for insertion into the ear canal.

23. A method for detecting biological material in an ear of a subject comprising:
    inserting a probe into an ear canal;
    illuminating the biological material at a site within the ear canal with light from a spectral excitation light source, the light being coupled to the biological material with one or more light delivery optical fibers, the one or more light delivery optical fibers located within the probe;
    collecting light from the biological material with one or more light collection optical fibers, the one or more light collection optical fibers located within the probe;
    imaging tissue within the ear canal with an imaging detector;

detecting the collected light with a spectral detector optically coupled to a spectrometer, the spectrometer coupled to the one or more light collection optical fibers to receive Raman light from the biological material in the ear canal;

processing the detected Raman scattered light with a data processor to determine a spectral contribution of a plurality of endogenous molecular components within the biological material including at least one molecular component selected from the group of mucin, keratin, apatite, and collagen in the detected Raman scattered light, the data processor generating spectral data corresponding to at least a first principal component and a second principal component that are scored to record a biochemical characteristic of the biological material at the site within the ear canal and thereby generate diagnostic data regarding a pathological condition of the ear based on stored spectral markers corresponding to a plurality of different pathological conditions of endogenous tissue, wherein the spectral markers comprise a cluster map of principle component data; and displaying, on a display that is connected to the data processor, the image of the tissue within the ear canal and the diagnostic data to indicate at least one of the plurality of pathological conditions based on the generated spectral data and the stored spectral markers.

24. The method of claim 23 further comprising detecting light through a sapphire window at a distal end of the probe.

25. The method of claim 23 further comprising filtering light with one or more optical filters wherein at least one filter is located at a distal end of the one or more light delivery optical fibers.

26. The method of claim 23 further comprising filtering light with one or more optical filters including a long-pass filter located at a distal end of the one or more light collection optical fibers.

27. The method of claim 23, wherein the spectral data includes at least one of fluorescence spectra, Raman spectra, and reflectance spectra.

28. The method of claim 23 further comprising viewing a middle ear anatomical feature with the imaging detector of the probe, the probe comprising an otoscope or otoendoscope.

29. The method of claim 28 further comprising viewing a tympanic membrane through the otoscope.

30. The method of claim 23 further comprising diagnosing a condition of the biological material including at least one of a cholesteatoma, myringosclerosis, or otitis media.

31. The method of claim 23 wherein the biological material comprises one or more of keratin, collagen, nicotinamide adenine dinucleotide (NADH), elastin, tryptophan, flavin adenine dinucleotide (FAD), mucin, or porphyrins.

32. The method of claim 23 wherein the biological material is one or more blood analytes.

33. The method of claim 32 wherein the blood analyte is glucose.

34. The method of claim 28 wherein the imaging detector is configured to acquire white-light images of a region of interest within the ear canal.

35. The method of claim 23 wherein the probe is a speculum, the speculum including the one or more light delivery optical fibers and the one or more light collection optical fibers.

36. The method of claim 23 further comprising filtering light from the spectral excitation light source using one or more filters mounted on a filter wheel positioned within the device.

37. The method of claim 23 wherein the spectral excitation light source is one or more of a laser or a light emitting diode (LED).

38. The method of claim 23 further comprising determining a disease diagnosis of a fluid component of tissue within the middle ear.

* * * * *